US009389230B2

(12) United States Patent
Ma et al.

(10) Patent No.: US 9,389,230 B2
(45) Date of Patent: Jul. 12, 2016

(54) IDENTIFICATION OF SECRETED PROTEINS AS DETECTION MARKERS FOR CITRUS DISEASE

(71) Applicant: The Regents of the University of California, Oakland, CA (US)

(72) Inventors: Wenbo Ma, Riverside, CA (US); Georgios Vidalakis, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/829,270

(22) Filed: Mar. 14, 2013

(65) Prior Publication Data

US 2014/0127718 A1 May 8, 2014

Related U.S. Application Data

(60) Provisional application No. 61/615,760, filed on Mar. 26, 2012.

(51) Int. Cl.
*G01N 33/569* (2006.01)
*C07K 16/12* (2006.01)
*G01N 21/84* (2006.01)

(52) U.S. Cl.
CPC ...... *G01N 33/56911* (2013.01); *C07K 16/1264* (2013.01); *G01N 2021/8466* (2013.01)

(58) Field of Classification Search
CPC .................................................. C07K 16/1264
See application file for complete search history.

(56) References Cited

PUBLICATIONS

Ariovich et al., The use of immuno-gold staining techniques for detection of bacterium associated with greening diseased citrus, Phytopathology, 79, (1989), p. 382-384.*
Das ("Rapid detection of Candidatus Liberibacter asiaticus, the bacterium associated with citrus Huanglongbing (Greening) disease using PCR", Current Science, 87(9), (2004), p. 1183-1185.*
Garnier et al., Study of the Greening organism (GO) with monoclonal antibodies: Serological Identification, Morphology, Serotypes and Purification of GO, (1991) p. 428-435.*
National Academy of Science (referred to as NAS), Destructive citrus disease affecting Florida could be combated with bacteria-resistant trees, early detection. Science Daily. (2010). Web. Accessed Jul. 29, 2014. <http://www.sciencedaily.com/releases/2010/03/100323105956.htm>.*
Loewenstein et al., Drought tolerance, xylem sap abscisic acid and stomatal conductance during soil drying: a comparison of young plants for temperate deciduous angiosperms, Tree Physiology, 18, (1998), p. 421-430.*
Ma & Vidalakis, CRB Project Plan—Research Grant Proposal for FY 2010-2011, Identification of Spiroplasma citri secreted proteins as detection markers for citrus stubborn disease ; pp. 1-9 Web: http://www.citrusresearch.org/wp-content/uploads/5300-139-Ma-Proposal-2010-2011.pdf [Accessed on Apr. 16, 2015].*
"Evaluation of citrus stubborn disease detection markers," Citrus Advanced Technology Program, submitted Feb. 15, 2011, Quarterly Report. Retrieved from the internet at research.citrusrdf.org/reports/2011/02/15/quarterly-report-form-2010-ar2.pdf on Nov. 4, 2014.

* cited by examiner

*Primary Examiner* — Christine Foster
*Assistant Examiner* — Ellen J Marcsisin
(74) *Attorney, Agent, or Firm* — Kilpatrick Townsend & Stockton LLP

(57) ABSTRACT

Secreted proteins as detection markers for insect vector and graft transmitted citrus disease are described. Method and kits for detecting the secreted proteins are provided.

6 Claims, 4 Drawing Sheets

Lane 1: *S. citri* bacterial cells

Lane 2: graft-inoculated citrus tissue

Lane 3: healthy citrus tissue

Lane 4-8: five CSD-infected trees from the field

| Sample | Q-PCR | IMPRINT |
|---|---|---|
| -ve control | - | - |
| +ve control (1) | + | + |
| +ve control (2) | + | + |
| +ve control (2) | + | + |
| Field sample 1 | + | + |
| Field sample 2 | - | + |
| Field sample 3 | - | - |
| Field sample 4 | + | + |
| Field sample 5 | - | + |
| Field sample 6 | + | + |
| Field sample 7 | + | + |
| Field sample 8 | + | + |
| Field sample 9 | + | + |

SEQUENCE LISTING

<160> NUMBER OF SEQ ID NOS: 35

<210> SEQ ID NO 1
<211> LENGTH: 411
<212> TYPE: PRT
<213> ORGANISM: Spiroplasma citri
<220> FEATURE:
<223> OTHER INFORMATION: Spiroplasma citri strain GII3-3X conserved
hypothetical lipoprotein transmembrane, locus
SPICI03_098, SCi00082

<400> SEQUENCE: 1

```
Met Arg Lys Leu Leu Ser Ile Phe Ala Ala Thr Thr Leu Val Thr Thr
 1               5                  10                  15

Ser Ala Ala Ser Ala Val Ala Cys Ser Gly Ala Pro Gln Gly Asn Leu
            20                  25                  30

Ile Pro Ile Phe Met Tyr Asn Gly Asn Gln Lys Phe Ser His Ala Pro
        35                  40                  45

Thr Val Thr Arg Lys Ser Ile Asn Gly Ile Asp Asp Val Thr Gln Ser
    50                  55                  60

Gly Lys Asp Glu Asn Gly Ala Pro Tyr Glu Tyr Ser Leu Gln Gly Gly
65                  70                  75                  80

Arg Met Gly Leu Ile Asn Gly Leu Ile Asn Asn Ala Ile Asn Pro Ile
                85                  90                  95

Leu Asn Gly Ile Asn Leu Thr Lys Asp Asn Ser Ala Thr Thr Gly Lys
            100                 105                 110

Gly Ala Lys Trp Thr Asp Glu Gln Ile Ala Ala Gly Leu Glu Gly Gln
        115                 120                 125

Lys Glu Gln Leu Val Gln Thr Ala Lys Thr Asp Ala Gln Asp Pro Phe
    130                 135                 140

Asn Ser Ser Lys Lys Ile Asn Gln Lys Ala Ile Trp Lys Asp Leu Phe
145                 150                 155                 160

Asn Asn Tyr Ser Thr Ser Phe Asp Ser Ser Tyr Ser Gln Val Ala Phe
                165                 170                 175

Leu Ala Asn Glu Asn Lys Ala Ile Leu Asn Lys Thr Asn Asp Asn Leu
            180                 185                 190

Val Thr Met Thr Gly Asn Ala Glu Lys Thr Asn Asn Lys Asn Trp Val
        195                 200                 205

Lys Glu His Thr Trp Pro Asp Gly Lys Lys Ser Pro Tyr Thr Pro Ser
    210                 215                 220

Ser Leu Lys Val Leu Ser Pro Ile Ala Ser Ile Leu Glu Trp Phe Asn
225                 230                 235                 240

Asp Pro Lys Asn Ser Tyr Asn Gln Gly Tyr Asn Gln Ile Asp Gln Asn
                245                 250                 255

Arg Gly Tyr Gln Ser Ala Arg Tyr Leu Ala Ile Ala Ile Pro Asn Val
            260                 265                 270

Thr Ile Arg Phe Glu Phe Gln Gly Glu His Asn Cys Phe Thr Phe Thr
        275                 280                 285

Val Thr Ile Asp Lys Leu Val Ala Tyr Ala Asn Tyr Leu Val Tyr Glu
    290                 295                 300

Asn Pro Asn Ser Thr Lys Asp Asn Pro Ser Tyr Gly His Gln Trp Phe
305                 310                 315                 320

Phe Leu Ser Tyr Gly Phe Tyr Asp Phe Glu Ser Leu Lys Asp Asp Asp
                325                 330                 335

Tyr His His Tyr Asn Phe Asn Ala Ile Pro Asp Asp Val Lys Ile Asp
            340                 345                 350
```

```
Lys Asn Ile Lys Val Ala Leu Gly Phe Phe Lys Lys Asn Asp Asp Lys
        355                 360                 365

Gly Ile Leu Thr Ala Asp Glu Asp Lys Glu Val Gly Lys Arg Gly Gln
    370                 375                 380

Phe Pro Thr Ala Glu Thr Asp Tyr Thr Phe Pro Ala Leu Lys Trp Lys
385                 390                 395                 400

Ile Asn Val Asn Ser Ile Thr Asp Gln Tyr Lys
                405                 410


<210> SEQ ID NO 2
<211> LENGTH: 566
<212> TYPE: PRT
<213> ORGANISM: Spiroplasma citri
<220> FEATURE:
<223> OTHER INFORMATION: Spiroplasma citri strain GII3-3X hypothetical
      lipoprotein transmembrane, locus SPICI20_066,
      SCi01168

<400> SEQUENCE: 2

Met Lys Lys Ile Leu Ser Ile Leu Gly Ala Met Ser Ile Leu Ser Ser
 1               5                  10                  15

Thr Gly Thr Ser Ile Tyr Ala Cys Thr Lys Lys Asp Phe Glu Arg Phe
            20                  25                  30

Thr Asp Pro Ala Ile Val Asp Glu Val Lys Arg Trp Ile Ile Ala Lys
        35                  40                  45

Ile Asn Ser Glu Asn Glu Ser Asn Val Val Lys Tyr Ser Phe Asn Asp
    50                  55                  60

Ile Phe Thr Lys Ala Ala Leu Lys Glu Met Thr Thr Arg Leu Leu Asp
65                  70                  75                  80

Thr Asn Ile Ser Lys Phe Phe Tyr Ala Ser Glu Glu Ala Thr Arg Ala
                85                  90                  95

Arg Tyr Thr Gly Val Thr Ile Asp Val Asn Gln Pro Asp Ser Leu Leu
            100                 105                 110

Ile Lys Gln Phe Ile Asn Phe Val Glu Gln Val Ala Leu Asp Asn Leu
        115                 120                 125

Ser Thr Lys Tyr Ser Thr Gly Ile Ser Asn Ser Thr Pro Leu Glu Thr
    130                 135                 140

Thr Ile Ala Gly Gln Gly Tyr Ala Pro Asp Tyr Gln Ser Glu Gly Trp
145                 150                 155                 160

Tyr Val Gly Gly Ser Gln Ser Tyr Phe Trp Lys Gly Thr Gly Lys Pro
                165                 170                 175

Asn Tyr Met Gln Ser Arg Lys Gly Gln Gly Glu Ala Asn Phe Glu Ile
            180                 185                 190

Lys Ser Lys Ser Ala Gly Ala Asn Tyr Thr Asp Phe Asn Ala Met Ser
        195                 200                 205

Glu Asp Asp Lys Lys Ala Ala Leu Lys Thr Arg Phe Lys Asp Tyr Tyr
    210                 215                 220

Thr His Val Glu Ile Pro Ala Val Ile Asp Lys Ile Ile Thr Ala Thr
225                 230                 235                 240

Tyr Leu His Gln Asn Glu Ile Lys Arg Tyr Gly Ser Gly Asn Asn Ser
                245                 250                 255

Ser Ile Tyr Leu Asn Arg Asn Ser Ala Leu Phe Asn Ala Leu Gln Ser
            260                 265                 270

Trp Asp Thr Ile Ser Gly Ala Arg Trp Lys Ser Tyr Ile Lys Met Val
        275                 280                 285
```

-continued

```
Trp Glu Leu Lys Leu Asp Lys Glu Glu Leu Asp Lys Leu Phe Ala Asp
    290                 295                 300

Lys Gly Pro Leu Ala Asn Val Glu Lys Leu Asn Ser Asp Leu Thr Asn
305                 310                 315                 320

Asn Gln Asp Ile Leu Met Lys Ile Leu Lys Glu Met Phe Asn Ala Lys
                325                 330                 335

Lys Asp Asn Ile Phe Asn Asn Met Ile Lys Asp Gly Ile Asp Pro Ile
            340                 345                 350

Phe Gly Ile Ser Gly Phe Lys Gly Phe Val Gly Ile Asp Lys Asn Lys
        355                 360                 365

Asn Pro Asn Asp Ile Phe Thr Thr Leu Asn Asn Ala Asp Ser Tyr Lys
    370                 375                 380

Gln Lys Val Ile Asp Thr Ala Thr Pro Gly Ile Ile Lys Ser Gly Glu
385                 390                 395                 400

Gly Thr Asp Pro Ser Ser Tyr Gln Phe Leu Asp Thr Asn Lys Arg Tyr
                405                 410                 415

Gly Ser Phe Val Leu Thr Leu Pro Ile Tyr Ala Val Asp Leu Met Lys
            420                 425                 430

Asn Met Asn Ile Asn Tyr Lys Asn Asp Asn Lys Asn Asn Lys Glu Leu
        435                 440                 445

Ser Leu Thr Trp Tyr Gly Ser Gly Gly Thr Pro Thr Asp Leu Asp Gln
    450                 455                 460

Ala Trp Leu Ala Gln Gln Gly Gly Ile Lys Arg Ser Leu Ser Trp Leu
465                 470                 475                 480

Tyr Asn Lys Lys Gly Tyr Leu Gly Thr Tyr Asp Glu Asn Gly Gln Pro
                485                 490                 495

Leu Tyr Asn Asp Asn Gly Thr Pro Val Asp Ile Thr Lys Asn Ile Lys
            500                 505                 510

Gly Gln Ile Leu Lys Trp Ile Glu Tyr Thr Phe Ala Lys Gln Gln Asn
        515                 520                 525

Leu Gln Thr Ala Ala Lys Thr Arg Leu Tyr Ser Leu Val Phe Ala Asn
    530                 535                 540

Asn Pro Glu Asn Val Tyr Ser Gln Thr Leu Tyr Asp Ala Ile Gly Ser
545                 550                 555                 560

Tyr Ile Ile Lys Glu Asp
                565


<210> SEQ ID NO 3
<211> LENGTH: 730
<212> TYPE: PRT
<213> ORGANISM: Spiroplasma citri
<220> FEATURE:
<223> OTHER INFORMATION: Spiroplasma citri strain GII3-3X hypothetical
      lipoprotein transmembrane, locus SPICI09_027,
      SCi01478

<400> SEQUENCE: 3

Met Arg Lys Leu Leu Asn Ile Leu Ala Ala Ala Thr Leu Ala Ala Thr
 1               5                  10                  15

Pro Ala Leu Thr Ala Ser Cys Lys Thr Lys Ala Lys Ser Ala Glu Asp
            20                  25                  30

Lys Tyr Lys Asp Ser Ser Val Glu Asn Leu Pro Asn Gly Pro Leu Lys
        35                  40                  45

Ser Lys Ile Leu Gln Thr Thr Leu Phe Thr Lys Ala Thr Ile Ala Asn
    50                  55                  60

Arg His Glu Asn Leu Asn Thr Tyr Thr Pro Ser Met Leu Gln Met Leu
```

-continued

```
65                  70                  75                  80

Met Arg Leu Pro Asp Ser Tyr Lys Asp Lys Asp Gly Asn Ile Val Asp
                85                  90                  95

Ile Asp Tyr Tyr Arg Gly Lys Tyr Leu Asn Lys Asn Asn Gly Met Pro
            100                 105                 110

Leu Thr Thr Leu Ser Ser Asn Tyr Asp Tyr Met Asn Leu Leu Asp Asn
        115                 120                 125

Glu Leu Tyr Asn Thr Glu Lys Gln Thr Lys Lys Lys Ile Ser Asp Tyr
    130                 135                 140

Ser Asp Lys Asp Pro Leu Pro Ser Ile Pro Asn Leu Thr Lys Asn Ser
145                 150                 155                 160

Asn Met Leu Asn Tyr Trp Tyr Asp Gly Gly Pro Leu Ser Asn Tyr Ser
                165                 170                 175

Ile Val Lys Glu Ile Leu Pro Thr Lys Cys Asp Asp Lys Arg Ile Asn
            180                 185                 190

Gln Asn Ile Val Asp Ala Cys Asn Lys Ala Ile Phe Glu Met Pro Arg
        195                 200                 205

Thr Thr Tyr Phe Tyr Asn Phe Asn Met Asp Tyr Ser Pro Met Ala Thr
    210                 215                 220

Lys Asp Ile Lys Phe Asp Thr Asp Thr Asn Gln Asn Phe Ile Ile Asn
225                 230                 235                 240

Asn Gln Lys Phe Ala Ala Gly Gly Pro Phe Lys Thr Ala Gln Lys Ser
                245                 250                 255

Glu Glu Gln Asp Lys Leu Ser Ile Ile Leu Gln Leu Ile Ser Met Ala
            260                 265                 270

Asp Met Phe Thr Asp Arg Ser Gln Ser Lys Thr Tyr Ile Asn Gln Leu
        275                 280                 285

Asn Lys Phe Leu Ala Leu Ser Gly Asp Ser Asp Gly Thr Phe Met Gly
    290                 295                 300

Ser Ile Leu Gly Ala Ile Tyr Tyr Gln Ile Phe Ala Ser Pro Lys Leu
305                 310                 315                 320

Pro Asn Asp Pro Thr Lys Glu Asn Ala Asn Tyr Thr Phe Ala Lys Leu
                325                 330                 335

Gly Val Thr Lys Ala Leu Gln Leu Leu Arg Lys Asp Ser Thr Glu Arg
            340                 345                 350

Gln Ala Ile Lys Gln Lys Ile Asp Val Phe Phe Asp Ala Gln Ser Gln
        355                 360                 365

Val Phe Ser Asp Leu Leu Ala Val Arg Pro Met Gln Pro Gly Leu Asp
    370                 375                 380

Leu Asn Lys Pro Glu Gly Gln Tyr Lys Asn Arg Asp Ala Met Trp Asn
385                 390                 395                 400

Gly Lys Thr Pro Asn Leu Arg Leu Val Asp Leu Leu Phe Lys Lys Asp
                405                 410                 415

Ala Ser Thr Lys Ser Leu Ala Glu Leu Phe Thr Asp Phe Gly Glu Tyr
            420                 425                 430

Leu Asp Asp Leu Tyr Thr Lys Ala Asp Val Glu Cys Gln Glu Glu Ala
        435                 440                 445

Asn Asn Ser Ile Ser Ser Phe Leu Lys Leu Ala Ala Asn Val Val Thr
    450                 455                 460

Pro Gly Phe Lys Val Val Leu Gln Ser Met Ser Lys Met Met Leu Ser
465                 470                 475                 480

Lys Ser Glu Gly Gly Leu Gly Thr Leu Ser Val Asn Asp Ile Asn Arg
                485                 490                 495
```

-continued

```
Phe Val Val Ala Leu Ser Lys Gly Ile Leu Gln Ser Ala Asn Ala Leu
            500                 505                 510

Thr Glu Val Ser Lys Leu Pro Trp Ser Glu Ala Thr Asp Gln Glu Gln
        515                 520                 525

Asn Gln Thr Lys Ile Thr Gln Leu Leu Thr Gly Ser Asp Asp Pro Ser
    530                 535                 540

Thr Pro Thr Lys Asp Ser Phe Met Asp Leu Ala Phe Thr Trp Phe Asn
545                 550                 555                 560

Asp Ser Thr Gln Pro Val Arg Ala Leu Leu Asn Lys Leu Tyr Phe Asp
                565                 570                 575

Pro Asp Ser Glu Thr Arg Lys Asp Leu Leu Ala Ile Asn Asn Ala Leu
            580                 585                 590

Tyr Glu Tyr Ser Asn Asn Leu Leu Leu Gly Ala Asn Trp Asn Ile Ser
        595                 600                 605

Asn Gly Gln Leu Glu Glu Asn Lys Leu Ser Tyr Asp Ile Glu Tyr Lys
    610                 615                 620

Gly Thr Gly Asp Ala Asp Val Val Ala Asn Leu Asp Leu His Gln Asn
625                 630                 635                 640

Trp Tyr Ile Pro Lys Ser Glu Ile Lys Thr Tyr Gln Asp Leu Asn Ala
                645                 650                 655

Ala Tyr Leu Asn Ala Leu Gly Asn Arg Asp Leu Asp Trp Phe Met Lys
            660                 665                 670

Tyr Asp Gly Leu Gly Asn Asn Tyr Gln Lys Val His Tyr Lys Tyr Lys
        675                 680                 685

Val Thr Trp Met Asn Ile Asn Pro Gly Asp Asp Ser His Gln Tyr Trp
    690                 695                 700

Val Ile Ser Asn Ile Gln Trp Phe Ala Lys Asp Ile Ser Gly Gln Trp
705                 710                 715                 720

Lys Arg Tyr Tyr Asp Ala Ile Glu Asn Asp
                725                 730


<210> SEQ ID NO 4
<211> LENGTH: 291
<212> TYPE: PRT
<213> ORGANISM: Spiroplasma citri
<220> FEATURE:
<223> OTHER INFORMATION: Spiroplasma citri strain GII3-3X hypothetical
      lipoprotein transmembrane, locus SPICI19_098,
      SCi01257

<400> SEQUENCE: 4

Met Lys Trp Leu Leu Thr Leu Phe Ser Val Phe Val Leu Gly Phe Gly
 1               5                  10                  15

Ser Ser Leu Gly Val Val Ser Cys Thr Val Arg Ala Lys His Glu Pro
            20                  25                  30

Asp Asp Asn Asp Glu Leu Asp His Asn Gln Asp Leu Glu Ile Leu Asn
        35                  40                  45

Gln Ile Lys Lys Glu Ala Lys Gln Thr Leu Ser Thr Trp Trp Gln Thr
    50                  55                  60

Lys Thr Met Ile Asp Ile Ile Lys Asp Tyr Gln Glu Gln Ile Ser Ser
65                  70                  75                  80

Phe Lys Glu Leu Val Thr Gln Val Lys Thr Lys Asn Asp Gly Ser Leu
                85                  90                  95

Thr Leu Thr Ser Ile Ala Ile Ser Lys Tyr Cys Phe Leu Asn Gln Leu
            100                 105                 110
```

```
Leu Ile Gly Phe Lys Ala Glu Phe Asn Asn Leu Asn Gln His Leu Gln
        115                 120                 125

Asn Arg Tyr Ser Asn Tyr Tyr Val Asp Thr Met Pro Leu Phe Leu Gly
    130                 135                 140

Glu Asn Asp Ile Ser Phe Asn Leu Tyr Asn Ile Asn Phe Asp Lys Ile
145                 150                 155                 160

Ala Lys Leu Leu Ala Asp Thr Ala Gln Ala Val Leu Gly Ile Thr Val
                165                 170                 175

Gln Val Asn Ile Ala Tyr Glu Val Arg Phe Lys Gly Leu Pro Thr Glu
            180                 185                 190

Asp Asn Ile Gln Val Ser Ile Thr Thr Thr Asn Asp Ser Glu Val Leu
        195                 200                 205

Asn Asn Ile Gln Asp Lys Val Glu Asn Tyr Phe Val Asn Phe Leu Asp
    210                 215                 220

Thr Ile Phe Lys Ala Lys Asn Tyr Arg Ile Ile Ser Lys Gln Phe Asn
225                 230                 235                 240

Ile Lys Thr Asp Ile Val Trp Pro Ile Ile Ser Lys Glu Leu Asn Asp
                245                 250                 255

Arg Asn Ile Ser Phe Gln His Ile Ile Phe Asn Phe Leu Tyr Tyr Gly
            260                 265                 270

Gln Gln Ile Tyr Leu Ile Phe Ile Pro Leu Asn Ile Trp Thr Leu Thr
        275                 280                 285

Arg Leu Phe
    290


<210> SEQ ID NO 5
<211> LENGTH: 308
<212> TYPE: PRT
<213> ORGANISM: Spiroplasma citri
<220> FEATURE:
<223> OTHER INFORMATION: Spiroplasma citri strain GII3-3X hypothetical
      protein, locus SPICINP12_013, SCi01576

<400> SEQUENCE: 5

Met Ala Lys Ile Gly Gly Lys Ser Ser Ile Ala Leu Pro Thr Leu Phe
 1               5                  10                  15

Glu Ile Gly Gly Asn Ser Pro Thr Glu Lys Ala Ile Gly Asp Val Ala
            20                  25                  30

Val Leu Gln Ile Lys Lys Ile Leu Glu Ala Asp Ser Gln Tyr Ile Asp
        35                  40                  45

Ala Thr Glu Met Met Met Met Ser Ala Lys Gln Ile Ser Met Glu Asp
    50                  55                  60

Gly Phe Glu Gln Gly Gln Tyr Val Phe Pro Glu Arg Met Val Trp Gly
65                  70                  75                  80

Asn Asp Tyr Asp Ser Ser Ala Gly Ala Glu Gln Gln Ser Val Gly Val
                85                  90                  95

Arg Arg Ala Thr Val Met Met Asp Gln Met Leu Thr Phe Lys Tyr Asp
            100                 105                 110

Val Pro Ser Phe Asp Thr Val Arg Phe Met Glu Ser Pro Val Glu Val
        115                 120                 125

Arg Thr Asn Thr Ile Gly Glu Trp Met Arg Thr Ile Thr Arg Asn Trp
    130                 135                 140

Tyr Ser Asn Met Asn Ala Ile Tyr Leu Gln Gly Val Ile Asp Ser Cys
145                 150                 155                 160

Ile Ala Thr Gly Gln Tyr Ile Ile Leu Pro Ile Pro Thr Asp Ala Asp
                165                 170                 175
```

```
Ser Ala Gln Gln Thr Phe Tyr Lys Ile Asn Asp Ile Ala Ile Asn Leu
            180                 185                 190

Val Gln Lys Ile Asn Ala Leu Met Phe Gly Thr Lys Lys Glu Asp Leu
        195                 200                 205

Met Val His Val Ala Met Pro Ala Phe Ala Gln Phe Thr Lys Ala Tyr
    210                 215                 220

Thr Lys Ile Leu Asp Gln Ile Ala Ala Asp Thr Leu Ala Thr Gly Gln
225                 230                 235                 240

Leu Trp Arg Lys Met Ile Val Gly Val Asp Val Phe Glu Ser Trp Tyr
                245                 250                 255

Leu Gly Arg Gln Phe Asn Lys Gly Lys Glu Thr Gly Ile Asn Lys Asp
            260                 265                 270

Leu Asp Phe Asn Leu Asn Phe Ser Gln Thr Val Gly Ala Trp Gly Phe
        275                 280                 285

Ile Gly His Lys Glu Asp Cys Ala Met Pro Gln Gly Trp Lys Ser Ile
    290                 295                 300

Gln Gln Val Asn
305


<210> SEQ ID NO 6
<211> LENGTH: 373
<212> TYPE: PRT
<213> ORGANISM: Spiroplasma citri
<220> FEATURE:
<223> OTHER INFORMATION: Spiroplasma citri strain GII3-3X hypothetical
      lipolytic enzyme gdsl family protein, locus
      SPICI05_013, SCi01870

<400> SEQUENCE: 6

Met Lys Arg Phe Phe Thr Leu Leu Ala Val Leu Asn Val Ala Thr Gly
 1               5                  10                  15

Ser Thr Val Met Val Ala Ser Phe Thr Ile Ala Gln Gly Ala His Leu
            20                  25                  30

Asn Pro Val Asp Ser Leu Leu Leu Ile Gly Lys Asp Ile Asp Thr Ser
        35                  40                  45

Lys Ala Ile Asp Asp Ala Lys Ser Asn Leu Gln Phe Thr Asn Tyr Tyr
    50                  55                  60

Ile Leu Gly Asp Ser Leu Ser Asp Ser His Gly Ile Glu Lys Leu Val
65                  70                  75                  80

Lys Asn Ser Phe Lys Leu Asp Ile Lys Ile Gly Thr Asn Asp Pro Asn
                85                  90                  95

Asn Leu Glu Asn Tyr Gln Asn Gly Ser Leu Ser Asn Gly Asn Thr Ala
            100                 105                 110

Ala Val Leu Leu Asn Ala Lys Leu Gly Phe Asp Lys Ile Arg Pro Gly
        115                 120                 125

Ile Pro Asn Asp Tyr Ala Gly Asp Phe Gly Arg Asn Tyr Ala Ile Gly
    130                 135                 140

Gly Ala Thr Ala Val Asp Val Val Gly Thr Ala Gly Met Leu Leu Asn
145                 150                 155                 160

Arg Val Thr Ile Glu Lys Gln Ala Gln Ala Leu Val Ser Gln His Lys
                165                 170                 175

Leu Arg Ser Thr Asp Leu Val Leu Phe Glu Ile Gly Gly Asn Asp Leu
            180                 185                 190

Phe Gln Ile Ile Asp Thr Thr Asp Pro Gln Thr Glu Leu Glu Leu Met
        195                 200                 205
```

-continued

```
His Gln Ser Val Glu Arg Ile Lys Ile Ala Leu Phe Thr Leu Leu Asn
    210                 215                 220

Asn Gly Ile Arg Lys Ile Leu Phe Ser Asp Ala Pro Asn Val Ser Ala
225                 230                 235                 240

Ile Pro Arg Tyr Asn Asn Gln Asn Thr Asp Asp Thr Leu Lys Lys Arg
                245                 250                 255

Ala Asn Asn Ile Ser Thr Glu Phe His Ala Arg Val Ala Lys Met Ile
            260                 265                 270

Glu Leu Ala Asn Thr Tyr Tyr Lys Asn Ala Ile Arg Asn Trp Gly Leu
        275                 280                 285

Tyr Asp Asn Leu Ser Val Leu Met Thr Glu Phe Lys Ala Arg His Pro
    290                 295                 300

Lys Gly Asn Ile Thr Val Asn Phe Asn Asn Leu Asn Leu Asp Phe Ile
305                 310                 315                 320

Lys Ile Ile Glu Glu Lys Met Leu Asn Ala Gln Arg Asn Pro Ala Leu
                325                 330                 335

Pro Ala Asn Ala Asn Ile Asp Asp Tyr Phe Phe Phe Asp Ile Val His
            340                 345                 350

Pro Thr Arg Glu Val His Gln Leu Ala Met Glu His Tyr Tyr Gln Thr
        355                 360                 365

Ile Lys Glu Trp Thr
    370


<210> SEQ ID NO 7
<211> LENGTH: 463
<212> TYPE: PRT
<213> ORGANISM: Spiroplasma citri
<220> FEATURE:
<223> OTHER INFORMATION: Spiroplasma citri strain GII3-3X putative
      protein p123 N-terminal truncated, P123 protein variant A,
      locus SPICINP12_018, SCi01581

<400> SEQUENCE: 7

Met Leu Arg Gln Phe Gly Gly Leu Ile Gly Ser Asn Ser Leu Thr Phe
 1               5                  10                  15

Gly Cys Met Leu Lys Leu Thr Asp Lys Ile Lys Thr His Tyr Tyr Ser
            20                  25                  30

Ala Thr Gly Gln Asp Leu Gly Thr Lys Val Tyr Ser Thr Ile Asp Leu
        35                  40                  45

Gly Gln Asn Arg Ile Asn Val Asn Gly Gly Thr Asp Glu Ile Val Ile
    50                  55                  60

Leu Ser Gln Asp Phe Gln Ala Leu Asp Lys Asp Thr Pro Leu Thr Asn
65                  70                  75                  80

Leu Asp Asn Lys Leu Asp Phe Asn Pro Thr Val Asp Gly Thr Leu Glu
                85                  90                  95

Ser Tyr Val Ile Asp Leu Ile Asn Leu Gln Thr Ile Gly Lys Thr Asn
            100                 105                 110

Phe Lys Ile Thr Thr Tyr Ser Glu Asn Pro Phe Thr Leu Asn Asp Asn
        115                 120                 125

Ile Thr Ala Phe Gln Asn Phe Gln Gly Glu Trp Gln Thr Met Ala Lys
    130                 135                 140

Phe Ile Lys Pro Asn Gly Asn Val Gln Ala Trp Asn Ser Val Ile Lys
145                 150                 155                 160

Thr Ser Ala Leu Asp Tyr Asp Leu Leu Glu Glu Thr Thr Phe Phe Tyr
                165                 170                 175

Pro Gln Ala Val Leu Pro Pro Asp Pro Phe Thr Tyr Lys Pro Tyr Thr
```

```
            180                 185                 190

Val Asn Ile Leu Asp Ser Asn Thr Ile Lys Pro Leu Lys Ala Asn Ile
        195                 200                 205

Thr Ala Ala Lys Gln Cys Thr Ser Ser Ile Ser Phe Ile Trp Gln Lys
    210                 215                 220

Asp Trp Ile Asn Leu Phe Asn Asn Lys Tyr Asp Asn Val Tyr Tyr Glu
225                 230                 235                 240

Leu Glu Val Asp Leu Lys Gln Ile Asn Thr Thr Ile Thr Thr Trp Glu
                245                 250                 255

Gln Leu Leu Asn Ala Tyr Ser Ser Ile Gln Phe Asn Asn Leu Asn Asn
            260                 265                 270

Leu Gln Val Lys Cys Ala Pro Pro Asn Ile Glu Asn Phe Ile Pro Asn
        275                 280                 285

Arg Asn Ile Asn Ile Leu Gly Gly Tyr Ser Thr Cys Glu Asn Asn Leu
    290                 295                 300

Gly Trp Phe Ser Asn Gly Lys Leu Lys Val Lys Gly Asp Lys Gln Ile
305                 310                 315                 320

Asp Lys Val Asn Phe Asn Gly Ser Leu Ile Tyr Asp Leu Ala Asn Ile
                325                 330                 335

Lys Glu Asn Lys Lys Thr Thr Leu Phe Thr Gly Glu Thr Thr Gly Leu
            340                 345                 350

Pro Ser Gly Tyr Tyr Gln Asn Arg Tyr Ser Phe Ser Lys Asn Cys Asp
        355                 360                 365

Phe Ser Phe Leu Leu Gln Ile Thr Lys Leu Ser Asp Asn Asp Asp Asn
    370                 375                 380

Lys Ile Lys Glu Leu Tyr Val Gln Ala Trp His Thr Asn Asp Met Lys
385                 390                 395                 400

Leu Lys Ile Arg Phe Thr Lys Val Val Phe Pro Asp Phe Ser Phe Tyr
                405                 410                 415

Tyr Ser Asp Met Pro Val Val Lys Leu Tyr Lys Tyr Phe Gly Asn Asp
            420                 425                 430

Lys Asn Ile Ser Ile Asp Ile Asp Asn Ser Asn Ile Leu Gly Ile Arg
        435                 440                 445

Asn Asp Ser Ile Asn Pro Ile Ser Ile Thr Phe Ile Pro Arg Ser
    450                 455                 460


<210> SEQ ID NO 8
<211> LENGTH: 1067
<212> TYPE: PRT
<213> ORGANISM: Spiroplasma citri
<220> FEATURE:
<223> OTHER INFORMATION: Spiroplasma citri strain BR3-3X P123 protein,
      P123 protein variant B, locus SPICINP12_018, SCi01581

<400> SEQUENCE: 8

Met Ser Arg Ile Asn Pro Ser Val Met Glu Glu Leu Arg Arg Gln Ala
 1               5                  10                  15

His Asp Thr Leu Ile Asp Ile Arg Glu Asn Ile Arg Asp Asn Arg His
            20                  25                  30

Trp Met Val Phe Pro Phe Asn Val Tyr Ser Ser Tyr Ile Pro Asp Thr
        35                  40                  45

Glu Thr Gly Trp Lys Pro Asn Asn Ala Lys Pro Ser Asp Tyr Gly Ser
    50                  55                  60

Tyr Thr Arg Ile Phe Asp Asn Met Glu Ser Thr Ile Ala Gln Trp Gln
65                  70                  75                  80
```

-continued

```
Gly Ser Leu Lys Ile Val Gln Lys Tyr Lys Gly Glu Glu Ile Asn Ile
                85                  90                  95

Leu Thr Ile Asp Asp Phe Asn Lys Gln Pro Ile Asn Ser Thr Ile Trp
            100                 105                 110

Ala Asn Asn Glu Thr Pro Phe Ala Ile Lys Leu Lys Asp Glu Asn Glu
        115                 120                 125

Asn Asn Tyr Trp Lys Leu Ile Asp Gly Glu Asn Ile Tyr Asp Ile Asn
    130                 135                 140

Lys Met Leu Glu Tyr Leu Lys Gln Tyr Lys Leu Ser Tyr Phe Ile Asn
145                 150                 155                 160

Asn Asp Asn Lys Ala Asp Asn Phe Tyr Thr Lys Glu Val Lys Val Gly
                165                 170                 175

Lys Tyr Trp Asp Ala Tyr Met Ile Asp Asp Arg Ser Ser Ile Gln Phe
            180                 185                 190

Gly Asp Ala Lys Phe Glu Gln Val Phe Thr Gln Gln Ser Thr Glu Arg
        195                 200                 205

Gln Tyr Thr Leu Leu Ile Leu Asp Glu Asp Ala Glu Lys Leu Asn Ile
    210                 215                 220

Asn Asp Tyr Tyr Asn Phe Tyr Thr Val Phe Asn Asp Arg Gly Leu Asn
225                 230                 235                 240

Ile Gly Gly Gly Asp Ile Asn Ser Ala Pro Gln Asp Arg Gln Trp Leu
                245                 250                 255

Tyr Pro Ser Asn Val Ile Asn Tyr Tyr Ser Pro Tyr Asp Gly Ser Phe
            260                 265                 270

Leu Trp Gln Glu Ile Thr Phe Ser Ser Ile Asn Asp Lys Ile Ser His
        275                 280                 285

Ser Gly Leu Ser Val Arg Gln Phe Ile Gln Thr Ser Ala Pro Gly Glu
    290                 295                 300

Gly Tyr Cys Phe Pro Lys Ile Thr Tyr Asp Lys Lys Leu Asn Lys Gly
305                 310                 315                 320

Ile Val Glu Leu Asp Glu Val Leu Leu Lys Asp Pro Gly Val Arg Ala
                325                 330                 335

Met Ala Val Lys Phe Tyr Gly Asn Pro Ile Leu Phe Asp Met Pro Val
            340                 345                 350

Ile Gly Arg Pro Ile Ile Lys Gly Glu Phe Asn Lys Lys Val Met Asn
        355                 360                 365

Ser Arg Asp Leu Leu Met Tyr Asn Met Tyr Pro Ala Pro Pro Asp Lys
    370                 375                 380

Ile Asn Thr Tyr Ala Ala Pro Glu Val Ser Trp Tyr Asn Ile Gln Gly
385                 390                 395                 400

Ile Gln Pro Thr Met Ile Thr Gly Tyr Glu Asp Trp Lys Lys Asp Met
                405                 410                 415

Glu Ser Arg Tyr Asp Phe Trp Asn Gln Lys Asn Ser Glu Gly Ile Val
            420                 425                 430

Ile Thr Asp Lys Val Thr Ser Thr Ala Thr Asn Pro Thr Val Gly Thr
        435                 440                 445

Thr Ile Asn Glu Glu Asp Asn Asn Ser Glu Phe Tyr Trp Ser Lys Ser
    450                 455                 460

Trp Lys Ile Thr Pro Pro Asn Lys Val Lys Val Asn Ser Gly Ser Val
465                 470                 475                 480

Asp Asn Ile Ile Ser Thr Gln Ala Ser Ser Tyr Phe Arg Arg Lys Asp
                485                 490                 495

Glu Phe Gly Asn Thr Val Gly Gln Val Gln Ile Glu Tyr Asn Lys Met
```

-continued

```
            500                 505                 510

Gly Ser Cys Asn Val Trp Asp Ile Leu Asn Ile Asn Asn Phe Ile Asn
        515                 520                 525

Arg Gln Ile Thr Val Leu Pro Leu Asn Tyr Thr His Lys Leu Val Phe
    530                 535                 540

Asn Pro Phe Thr Ile Pro Gly Gly Val Gly Lys Phe Leu Asn Phe Ile
545                 550                 555                 560

Ser Phe Gly Ile Pro Trp Gly Trp Val Ile Asn Gln Asp Lys Lys Thr
                565                 570                 575

Trp Pro Asn Phe Gln Trp Leu Asn Gly Phe Met Ser Ala Asn Val Tyr
            580                 585                 590

Ser Phe Tyr Asn Asp Ala Phe Trp Ser Glu Lys Ser Lys Gly Lys Gly
        595                 600                 605

Tyr Leu Pro Phe Glu Ile Phe Arg Glu Gln Gly Asn Asp Lys Val Gly
    610                 615                 620

Ala Ile Phe Gly Ala Asn Ala Thr Ser Leu Gly Phe Thr Thr Leu Leu
625                 630                 635                 640

Thr Asp Lys Cys Lys Gly Thr Val Tyr Thr Asn Asp Gly Lys Ile Thr
                645                 650                 655

Glu Gln Ile Thr Tyr Ser Thr Tyr Asn Leu Lys Gln Leu Asn Glu Lys
            660                 665                 670

Thr Asn Arg Ile Tyr Leu Ile Asn Glu Gln Thr Lys Ala Val Glu Ala
        675                 680                 685

Gln Thr Pro Val Ser Asp Ser Glu Lys Asp Asn Asp Cys Glu Phe Leu
    690                 695                 700

Gln Thr Pro Asp Gly Thr Asn Cys Ser Tyr Ile Ile Asp Met Phe Ser
705                 710                 715                 720

Ile Gln Ala Leu Tyr Lys Gly Asn Phe Glu Ile Ile Phe Tyr Ala Asp
                725                 730                 735

Asn Pro Tyr Thr Asn Asn Glu Glu Asp Tyr Leu Arg Leu Ser Val Trp
            740                 745                 750

Ser Phe Arg Gly Lys Thr Lys Ser Val Leu Asn Asn Tyr Leu Arg Asp
        755                 760                 765

Met Thr Thr Asn Tyr Lys Thr Ser Phe Leu Leu Pro His Asp Tyr Glu
    770                 775                 780

Ile Pro Thr Phe Asn Tyr Pro Gln Tyr Val Leu Pro Pro Val Pro Tyr
785                 790                 795                 800

Asn Tyr Gln Pro Tyr Thr Lys Asp Ile Met Pro Ala Gly Val Val Gln
                805                 810                 815

Thr Leu Lys Thr Lys Ile Thr Ala Pro Ala Gln Cys Lys Glu Asn Phe
            820                 825                 830

Pro Pro Val Asn Leu Phe Asp Asp Thr Ala Glu His Asn Ala Tyr Tyr
        835                 840                 845

Glu Thr Glu Ile Asp Leu Arg Gln Ile Asp Pro Thr Ile Gln Ser Ile
    850                 855                 860

Asp Lys Phe Lys Ser Ala Tyr Lys Thr Ile Glu Ile Ser Asn Leu Gly
865                 870                 875                 880

Asn Leu Gln Val Glu Cys Gly Pro Pro Asn Ile Glu Asn Phe Ile Pro
                885                 890                 895

Asn Arg Asn Val Asp Ile Leu Gly Gly Leu Asn Cys Asn Ile Asn Leu
            900                 905                 910

Gly Ser Leu Ala Asn Ile Thr Leu Gln Glu Ser Gly Arg Ser Gln Thr
        915                 920                 925
```

```
Asp Lys Val Asn Phe Asp Asn Ile Arg Thr Leu Tyr Thr Asn Asn Ile
    930                 935                 940

Thr Asn Glu Val Gln Thr Phe Glu Pro Ile Ala Tyr Thr Asn Gly Leu
945                 950                 955                 960

Gln Gly Asp Asp Tyr Glu Asn Arg Tyr Phe Ala Ser Asp Lys Arg Val
                965                 970                 975

Val Leu Asp Phe Leu Leu Gln Ile Thr Lys Leu Ser Asn Asn Asn Asp
            980                 985                 990

Asn Asp Lys Ile Lys Glu Thr Tyr Leu Gln Ala Tyr Tyr Thr Asn Asp
        995                 1000                1005

Val Lys Leu Lys Ile Arg Ile Ser Lys Ile Ile Asn Ile Asn Leu Leu
    1010                1015                1020

Leu Asp Ser Thr Met His Trp Lys Tyr Phe Gly Asn Asn Lys Asn Ile
1025                1030                1035                1040

Val Leu Asp Val Asp Asn Pro Asn Val Leu Gly Ile Arg Asn Lys Ser
                1045                1050                1055

Glu Asn Pro Val Lys Ile Thr Phe Ile Pro Arg
            1060                1065


<210> SEQ ID NO 9
<211> LENGTH: 98
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_00460

<400> SEQUENCE: 9

Met Arg His Leu Ile Leu Ile Met Leu Leu Ser Ile Leu Thr Thr Asn
 1               5                  10                  15

Ile Ala Arg Ala Gln Val Tyr His Ile His Ser Pro Arg Ile Ala Thr
            20                  25                  30

Lys Ser Ser Ile His Ile Lys Cys His Ser Cys Thr Leu Asn Lys His
        35                  40                  45

His Ile Asn Lys Thr Pro Ser Ser Ser Ser Ala Val Tyr Thr Lys Lys
    50                  55                  60

Glu Glu Leu Ile Asp Gly Lys Lys Ala Met Ile Thr Thr Asp Asn Phe
65                  70                  75                  80

Met Gly Gly Glu Pro Ile Thr Phe Ile Lys Tyr Leu Phe Glu Glu Asp
                85                  90                  95

Lys Lys


<210> SEQ ID NO 10
<211> LENGTH: 351
<212> TYPE: PRT
<213> ORGANISM: Candidatus Liberibacter asiaticus
<220> FEATURE:
<223> OTHER INFORMATION: Candidatus Liberibacter asiaticus strain psy62
      outer membrane protein CLIBASIA_00995

<400> SEQUENCE: 10

Met Gly Leu Lys Lys Phe Phe Leu Gly Thr Val Ala Val Ala Thr Ile
 1               5                  10                  15

Ile Ser Tyr Ser Glu Ser Phe Ala Tyr Val Arg Gly Lys Thr Ser Met
            20                  25                  30

Val Ser Asn Asn Arg Ala Arg Asn Arg Ser Ala Gly Lys Val Gly Asn
        35                  40                  45
```

-continued

```
Val Leu Pro His Ile Thr Lys Val Gly Gly Ser Leu Glu Lys Ser Leu
    50                  55                  60

Gln Ala Arg Tyr His Lys Leu Asn Gly Asn Asn Glu Phe Asn Ser Leu
65                  70                  75                  80

Ala Tyr Asp Ile Pro Val Lys Gly Asn Leu Glu Val Asn Ala Asn Ala
                85                  90                  95

Gly Asp Val Thr Gly Val Ala Lys Leu Lys Leu Ala Val Asp Asp Val
            100                 105                 110

Leu Ser Met Gln Phe Ala Glu Ser Asp Val Arg Ala Leu Ala Phe Thr
        115                 120                 125

Val Pro Ser Ser Lys Leu Ser Val Glu Glu Leu Ser Leu Ser Met Lys
    130                 135                 140

Gly Ala Arg Leu Gly Tyr Tyr Lys Ser Trp Ser Asp Glu Val Asn Pro
145                 150                 155                 160

Val Tyr Ser Pro Thr Thr Leu Tyr Asn Asp Ala Arg Gly Leu Asp Lys
                165                 170                 175

Met Met Ser Leu Ser Tyr Arg His Ser Phe Gly Leu Leu Lys Ala Gly
            180                 185                 190

Leu Ser Thr Asp Leu Leu Gln Lys Asp Gly Leu Lys Gln Val Leu Gly
        195                 200                 205

Ile Gly Tyr Met Ala Ser Tyr Ala Ile Gly Lys Ile Arg Ser Thr Val
    210                 215                 220

Thr Gly Gly Tyr Asp Ala Gly Thr Asn Asn Val Ala Ile Arg Ala Asn
225                 230                 235                 240

Ile Ser Ser Pro Val Ser Arg Ala Gly Thr Leu Asp Cys Gly Ala Val
                245                 250                 255

Trp Ala Ser Gly Asp Asn Ser Tyr Tyr Asp Lys Ser Lys Tyr Ser Val
            260                 265                 270

Phe Ala Gly Tyr Lys Phe Asp Val Ala Lys Ser Ile Thr Ile Ser Gly
        275                 280                 285

Gly Gly Gln Tyr Phe Gly Asp Ile Asn Lys Thr Gly Lys Asp Gly Trp
    290                 295                 300

Ser Ala Gly Ile Ser Ala Lys Tyr Met Ile Ser Ser Gly Leu Glu Ala
305                 310                 315                 320

Gln Ala Ser Val Ala Phe Asn Asp Asn Phe Val Lys Lys Gly Val Ala
                325                 330                 335

Ile Asp Lys Gly Val Asp Leu Ser Val Gly Leu Lys Lys Ser Phe
            340                 345                 350
```

```
<210> SEQ ID NO 11
<211> LENGTH: 309
<212> TYPE: PRT
<213> ORGANISM: Candidatus Liberibacter asiaticus
<220> FEATURE:
<223> OTHER INFORMATION: Candidatus Liberibacter asiaticus strain psy62
      substrate-binding region of ABC-type glycine betaine transport
      system CLIBASIA_01135, COG2113 ABC-type proline/glycine
      betaine transport systems, periplasmic components

<400> SEQUENCE: 11

Met Tyr Lys Ile Leu Ala Val Cys Leu Phe Leu Thr Thr Phe Ser Ile
 1               5                  10                  15

Ser Tyr Ala Arg Asp Ala Asp Ser Cys Thr Pro Val Arg Phe Ala Asp
            20                  25                  30

Thr Gly Trp Thr Asp Ile Ala Ala Thr Thr Ala Met Thr Ser Val Ile
        35                  40                  45
```

-continued

```
Leu Glu Glu Ile Leu Gly Tyr Lys Thr Asn Ile Lys Leu Leu Ala Val
    50                  55                  60

Pro Val Thr Phe Arg Ser Leu Lys Asn Lys Gly Ile Asp Ile Phe Met
65                  70                  75                  80

Gly Tyr Trp Tyr Pro Ser Leu Glu Lys Phe Ile Ala Pro Tyr Leu Glu
                85                  90                  95

Glu Gly Ser Ile Lys Leu Val Ala Glu Asn Leu Gln Gly Ala Lys Tyr
            100                 105                 110

Met Leu Ala Val Asn Asp Val Gly Phe Ala Leu Gly Ile Lys Ser Tyr
        115                 120                 125

Gln Asp Ile Ala Lys Tyr Lys Lys Glu Leu Gly Ala Lys Ile Tyr Gly
    130                 135                 140

Ile Glu Pro Gly Asn Glu Gly Asn Gln Arg Ile Leu Asp Met Ile Asn
145                 150                 155                 160

Asn Asn Lys Phe Ser Leu Lys Gly Phe Arg Leu Ile Glu Ala Ser Glu
                165                 170                 175

Leu Ala Ser Phe Ser Gln Ile Arg Arg Asp Gln Arg Asn Asn Ile Pro
            180                 185                 190

Ala Val Phe Leu Ser Trp Glu Pro His Pro Ile Asn Ser Asp Leu Asn
        195                 200                 205

Ile His Tyr Leu Pro Gly Gly Glu Glu Ile Ser Gly Phe Gly Glu Ala
    210                 215                 220

Ser Val Tyr Thr Val Val Arg Ser Asp Tyr Leu Asp Lys Cys Pro Asn
225                 230                 235                 240

Ile Ser Arg Leu Leu Lys Asn Ile Lys Phe Ser Val Ala Leu Glu Asn
                245                 250                 255

Glu Met Met Lys Leu Ile Leu Asn Asn Lys Gln Asp Arg Gln Phe Val
            260                 265                 270

Gly Arg Thr Met Leu Arg Thr His Pro Asp Leu Leu Lys Asn Trp Leu
        275                 280                 285

Ile Gly Val Thr Thr Phe Asp Gly Gln Asp Pro Ser Arg Gln Leu Glu
    290                 295                 300

Arg Phe Met Asn Asn
305


<210> SEQ ID NO 12
<211> LENGTH: 238
<212> TYPE: PRT
<213> ORGANISM: Candidatus Liberibacter asiaticus
<220> FEATURE:
<223> OTHER INFORMATION: Candidatus Liberibacter asiaticus strain psy62
      flagellar basal body L-ring protein CLIBASIA_01295, COG2063
      flagellar basal body L-ring protein, flgH

<400> SEQUENCE: 12

Met Tyr Arg Tyr Ser Phe Ile Val Leu Cys Tyr Ser Ser Leu Leu Phe
 1               5                  10                  15

Gly Cys His Ser Ser Ile Ser Glu Ile Thr Gly Ile Pro Gln Met Ser
            20                  25                  30

Pro Met Gly Ser Ser Leu Asp Glu Asn Asn Arg Met Pro Phe Leu Gly
        35                  40                  45

Ile Asp Phe Lys Asn Ser Asp Ser Thr Lys Lys Ser Tyr Ser Leu Trp
    50                  55                  60

Arg Asp Ser His Ala Ala Leu Phe Lys Asp Ser Arg Ala Leu Asn Val
65                  70                  75                  80

Gly Asp Ile Leu Thr Val Asp Ile Arg Ile Asp Asp Gln Ala Val Phe
```

```
                85                  90                  95

Asp Asn Gln Thr Gly Arg Ser Arg Asn Asn Ser Leu His Arg Lys Leu
            100                 105                 110

Ser Gly Gly Phe Ser Leu Phe Gly Gln Gln Thr Pro Gln Met Asn Gly
        115                 120                 125

Asn Leu Asn Tyr Asp Gly Gly Gly Ala Ser Ser Gly Lys Gly Ser Ile
    130                 135                 140

Ser Arg Ala Glu Lys Leu Asn Leu Leu Ile Ala Ala Ile Val Thr Ala
145                 150                 155                 160

Ile Leu Glu Asn Gly Asn Leu Ile Ile Ser Gly Ser Gln Glu Val Arg
                165                 170                 175

Val Asn Asp Glu Ile Arg Ser Leu Asn Val Thr Gly Ile Val Arg Pro
            180                 185                 190

Gln Asp Val Asp Ala His Asn Ser Val Ser Tyr Asp Lys Ile Ala Glu
        195                 200                 205

Ala Arg Ile Ser Tyr Gly Gly Lys Gly Arg Thr Thr Glu Leu Leu Arg
    210                 215                 220

Pro Pro Ile Gly His Gln Leu Ile Glu Asn Leu Ser Pro Leu
225                 230                 235
```

<210> SEQ ID NO 13
<211> LENGTH: 175
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_01300, COG3334
      uncharacterized conserved protein

<400> SEQUENCE: 13

```
Met Ile Leu Leu Pro Ile Ile Tyr Tyr Tyr Lys Lys Arg Asp Met Leu
 1               5                  10                  15

Ser Gln Leu Leu Phe Leu Leu Phe Phe Phe Leu Gln Gly Phe Ala Asn
            20                  25                  30

Gln Ser Tyr Gly Asp Pro Thr Leu Val Asp Arg Glu Ile Gln Gln Tyr
        35                  40                  45

Cys Thr Asn Val Ile Asp Ser Val Arg Glu Arg Asp Tyr Leu Ser Gln
    50                  55                  60

Lys Lys Val Leu Glu Asp Leu Gln Lys Asp Ile Glu Gln Arg Val Ile
65                  70                  75                  80

Leu Leu Glu Asn His Lys Lys Glu Tyr Asn Leu Trp Phe Gln Lys Tyr
                85                  90                  95

Asp Ser Phe Ile Met Ser Tyr Asn Lys Asn Ile Leu Asp Ile Tyr Lys
            100                 105                 110

Lys Met Asp Ser Asp Ser Ala Ala Leu Gln Leu Glu Gln Ile Asp Pro
        115                 120                 125

Asp Ile Ser Ser His Ile Leu Met Arg Leu Ser Pro Arg Gln Ser Ser
    130                 135                 140

Leu Ile Met Ser Lys Met Asn Pro Lys Ser Ala Thr Met Ile Thr Asn
145                 150                 155                 160

Val Val Ala Asn Met Leu Lys Phe Lys Lys Leu Lys Arg Ser Ser
                165                 170                 175
```

<210> SEQ ID NO 14
<211> LENGTH: 336
<212> TYPE: PRT
<213> ORGANISM: Candidatus Liberibacter asiaticus -continued
<220> FEATURE:
<223> OTHER INFORMATION: Candidatus Liberibacter asiaticus strain psy62
      peptidase S11, D-alanyl-D-alanine carboxypeptidase 1
      CLIBASIA_01600, COG1686 D-alanyl-D-alanine carboxypeptidase

<400> SEQUENCE: 14

```
Met Arg Gln Phe Leu Val Ile Ile Ala Met Ala Met Leu Ser Asn Ile
 1               5                  10                  15

Phe Pro Phe Leu Ser Ile Ala Glu Thr Asn Lys Leu Pro Tyr Tyr Thr
            20                  25                  30

Leu Leu Asp Thr Asn Thr Gly His Val Ile Ala Glu Asn Tyr Pro Asp
        35                  40                  45

His Pro Trp Asn Pro Ala Ser Leu Thr Lys Leu Met Thr Ala Tyr Val
    50                  55                  60

Val Phe Ser Phe Leu Lys Glu Lys Lys Ala Met Leu Thr Thr Pro Ile
65                  70                  75                  80

Thr Ile Ser Lys Asn Ala Ser Glu Tyr Pro Pro Ser Asn Ser Thr Phe
                85                  90                  95

Lys Lys Gly Ser Thr Met Thr Leu Asp Asn Ala Leu Lys Leu Leu Ile
            100                 105                 110

Val Lys Ser Ala Asn Asp Ile Ala Val Ala Ile Ala Glu Ser Leu Cys
        115                 120                 125

Lys Thr Glu Lys Lys Phe Val Gln His Met Asn Asn Thr Ser Lys Asn
    130                 135                 140

Leu Gly Leu Ser Ala Thr His Phe Met Asn Ala His Gly Val Val Gln
145                 150                 155                 160

His Gly His Tyr Thr Thr Ala Arg Asp Met Ala Ile Leu Ser Trp Arg
                165                 170                 175

Ile Lys Thr Asp Phe Pro Gln Tyr Met His Tyr Phe Gln Ile Lys Gly
            180                 185                 190

Leu Glu Ile Lys Gly Lys Lys Tyr Pro Asn Thr Asn Trp Ala Val Gly
        195                 200                 205

Thr Phe Leu Gly Ala Asp Gly Met Lys Thr Gly Phe Thr Cys Ala Ser
    210                 215                 220

Gly Phe Asn Ile Val Ala Ser Ala Ile Gln Gly Asp Gln Ser Leu Ile
225                 230                 235                 240

Ala Val Ile Leu Gly Ala Leu Asp Arg Asn Thr Arg Asn Lys Val Ser
                245                 250                 255

Ala Ser Leu Leu Ser Met Gly Phe Tyr Asn Lys Thr Asp Arg Lys Lys
            260                 265                 270

Ile Asn Tyr Ile Ile Lys Asp Phe Tyr Gln Gln Asn Leu Ser Asn Glu
        275                 280                 285

Val Pro Asn Ile Ser Glu Glu Val Cys Thr Thr Gln Lys Glu Ile Ile
    290                 295                 300

Asn Tyr Asn Thr Gln Met Lys Glu Ala Lys Asp Lys Glu Ser His Phe
305                 310                 315                 320

Ile Asp Phe Glu Lys Ile Thr Leu Leu Lys Asn Lys Ile Thr Lys Lys
                325                 330                 335
```

<210> SEQ ID NO 15
<211> LENGTH: 162
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_03230

<400> SEQUENCE: 15

Met Asn Phe Arg Ile Ala Met Leu Ile Ser Phe Leu Ala Ser Gly Cys
1 5 10 15

Val Ala His Ala Leu Leu Thr Lys Lys Ile Glu Ser Asp Thr Asp Ser
20 25 30

Arg His Glu Lys Ala Thr Ile Ser Leu Ser Ala His Asp Lys Glu Gly
35 40 45

Ser Lys His Thr Met Asn Ala Glu Phe Ser Val Pro Lys Asn Asp Glu
50 55 60

Lys Tyr Thr Ile Ser Ser Leu Thr Lys Lys Ile Glu Ser Asp Thr Asp
65 70 75 80

Phe Arg Arg Glu Lys Ala Thr Ile Ser Leu Ser Ala His Asp Lys Glu
85 90 95

Gly Ser Lys His Thr Met Asn Ala Glu Phe Ser Val Pro Lys Asn Asp
100 105 110

Glu Lys Tyr Thr Ile Ser Ala Cys Ala Ser Asp Asp Lys Gly Asn Lys
115 120 125

Ser Thr Leu Cys Val Glu Cys Pro Ser Pro Ser Thr Pro Gly Gln Tyr
130 135 140

Asp Leu Asn His Cys Ala Glu Cys Glu Asn Thr Thr Ser Lys Gly Leu
145 150 155 160

Cys Pro

<210> SEQ ID NO 16
<211> LENGTH: 474
<212> TYPE: PRT
<213> ORGANISM: Candidatus Liberibacter asiaticus
<220> FEATURE:
<223> OTHER INFORMATION: Candidatus Liberibacter asiaticus strain psy62 putative pilus assembly protein CLIBASIA_03070, COG4964 Flp pilus assembly protein, secretin CpaC

<400> SEQUENCE: 16

Met Arg Tyr Leu Gln Arg Thr Phe Phe Thr Met Met Ser Ile Phe Leu
1 5 10 15

Phe Ser Ser Asn Pro Ser Val Ala Lys Leu Pro Pro Ile Lys Glu Ala
20 25 30

Asn Ala Ala Val Ile Asn Ile Ser Asp Val Glu Ile Gly Lys Gly Lys
35 40 45

Lys Ile Ser Ile Gly Leu Asn Lys Val Ile Ile Leu Gln Val Pro Val
50 55 60

Asp Val Gln Asp Val Leu Val Ser Asp Pro Thr Lys Ala Asp Val Val
65 70 75 80

Val His Ser Pro Arg Thr Met Tyr Leu Phe Gly Lys Asn Val Gly Gln
85 90 95

Ala Asn Val Ile Leu Ile Gly His Asp Gly Lys Gln Met Leu Asn Leu
100 105 110

Asp Ile Leu Ile Glu Arg Asp Ile Ala His Leu Glu Met Thr Leu Arg
115 120 125

Arg Phe Ile Ala Asp Ser Asn Ile Arg Val Glu Met Val Ser Asp Thr
130 135 140

Val Val Leu His Gly Met Val Arg Thr Ile Gln Asp Ser Gln Arg Ala
145 150 155 160

Val Glu Leu Ser Glu Thr Phe Leu Ser Gln Ser Gly Arg Asn Gln Tyr
165 170 175

```
Ala Asn Ser Ser Ser Lys Lys Val Met Asn Leu Leu Asn Ile Ala Gly
            180                 185                 190

Glu Asp Gln Val Thr Leu Lys Val Thr Ile Ala Glu Val Arg Arg Asp
        195                 200                 205

Ile Leu Lys Gln Ile Gly Phe Gln His Ser Ile Thr Gly Ser Ser Ser
    210                 215                 220

Gly Pro Ser Lys Ser Phe Ala Ala Asp Phe Gly Gly Lys Phe Val Ser
225                 230                 235                 240

Glu Gly Gly Asp Phe Ser Val Lys Gly Val Leu Asp Arg Phe Ser Phe
                245                 250                 255

Glu Thr Val Leu His Ala Leu Glu Arg Ala Thr Ala Ile Arg Thr Leu
            260                 265                 270

Ala Glu Pro Thr Leu Thr Ala Ile Ser Gly Gln Ser Ala Ser Phe Thr
        275                 280                 285

Ser Gly Gly Gln His Leu Tyr Lys Thr Val Ser Ser Ser Thr Gly Ala
    290                 295                 300

Thr Ser Val Thr Thr His Asp Tyr Gly Val Val Leu His Phe Thr Pro
305                 310                 315                 320

Thr Val Leu Ser Pro Gly Arg Ile Gly Leu Arg Ile Gln Thr Glu Val
                325                 330                 335

Ser Glu Pro Val Ile Gly Val Asn Ala Gly Asp Met Pro Ser Tyr Arg
            340                 345                 350

Val Arg Lys Ala Asp Thr Thr Val Glu Leu Pro Ser Gly Gly Thr Ile
        355                 360                 365

Val Leu Ala Gly Leu Leu Lys Asp Asp Ile Gln Gln Leu Lys Glu Gly
    370                 375                 380

Ile Pro Leu Leu Ser Lys Ile Pro Ile Leu Gly Ala Leu Phe Arg Asn
385                 390                 395                 400

Ser Arg Phe Asn Arg Glu Glu Thr Glu Ile Phe Ile Ala Ala Thr Pro
                405                 410                 415

Phe Leu Val Lys Pro Val Ala Met Arg Asp Leu Ser Arg Pro Asp Asp
            420                 425                 430

His Tyr Ser Val Glu Asp Asp Ala Lys Ala Phe Phe Phe Asn Arg Val
        435                 440                 445

Asn Lys Ile Tyr Gly Pro Lys Glu Ala Ser Glu Val Glu Gly Gln Asn
    450                 455                 460

Tyr Lys Gly Ala Ile Gly Phe Ile Tyr Lys
465                 470
```

<210> SEQ ID NO 17
<211> LENGTH: 412
<212> TYPE: PRT
<213> ORGANISM: Candidatus Liberibacter asiaticus
<220> FEATURE:
<223> OTHER INFORMATION: Candidatus Liberibacter asiaticus strain psy62
hypothetical protein CLIBASIA_02610, COG3487
uncharacterized iron-regulated protein

<400> SEQUENCE: 17

```
Met Tyr Phe Ile Thr Ile Ile Ser Ile Val Phe Thr Leu Pro Ser His
 1               5                  10                  15

Ala Leu Ser Ile Val Pro Asn Val Ser Leu Glu Lys Val Leu Gln Asn
            20                  25                  30

Tyr Ala Thr Ile Ala His Ala Lys Tyr Glu Asp Ala Leu Met Cys Ala
        35                  40                  45

Arg Thr Leu Asp Ser Ala Ile Glu Thr Leu Val Thr Thr Pro Asn Lys
```

```
    50                  55                  60

Lys Asn Leu Glu Asn Ala Arg Leu Gln Trp Ile Arg Ala Arg Ile Pro
65                  70                  75                  80

Tyr Gln Gln Ser Glu Val Tyr Arg Phe Gly Asn Lys Ile Val Asp Thr
                85                  90                  95

Trp Asp Lys Lys Val Asn Ala Trp Pro Leu Asp Glu Gly Phe Ile Asp
            100                 105                 110

Tyr Val Asp Ser Ser Tyr Gly Lys Glu Asn Glu Glu Asn Asn Leu Tyr
        115                 120                 125

Thr Ala Asn Ile Ile Ala Asn Ser Lys Ile Ile Val Asn Glu Lys Glu
    130                 135                 140

Ile Asp Leu Ser Ile Ile Ser Pro Asp Leu Leu Arg Lys Leu His Arg
145                 150                 155                 160

Ala Asn Gly Ile Asp Thr Asn Ile Thr Thr Gly Tyr His Val Ile Glu
                165                 170                 175

Phe Leu Leu Trp Gly Gln Asp Leu Lys Thr Asn Val Arg Glu Pro Gly
            180                 185                 190

Asn Arg Pro Tyr Thr Asp Phe Asp Ile Gly Asn Cys Thr Gly Gly His
        195                 200                 205

Cys Arg Arg Arg Val Glu Tyr Leu Lys Val Val Ser Lys Ile Leu Val
    210                 215                 220

Ser Asp Leu Glu Glu Met Met Lys Ala Trp Gly Pro Asp Gly Gln Ala
225                 230                 235                 240

Thr Lys Asp Leu Met Lys Asp Ile Asn Ala Gly Leu Asn Ser Ile Ile
                245                 250                 255

Thr Gly Met Thr Ser Leu Ser Tyr Asn Glu Leu Ala Gly Glu Arg Met
            260                 265                 270

Asn Leu Gly Leu Ile Leu His Asp Pro Glu Gln Glu Ile Asp Cys Phe
        275                 280                 285

Ser Asp Asn Thr Tyr Ala Ser Tyr Leu Asn Asp Val Ile Gly Ile Ile
    290                 295                 300

Ser Ser Tyr Thr Gly Glu Tyr Ile Arg Met Asn Gly Glu Lys Ile His
305                 310                 315                 320

Gly Ala Ser Ile His Asp Leu Ile Ser His Asn Asn Arg Asn Leu Ala
                325                 330                 335

Gln Glu Ile Asn Asp Lys Phe Ser Asn Thr Met Lys Asp Phe His Ile
            340                 345                 350

Leu Lys Asp Arg Ala Glu Asn Ile Glu Ser Phe Asp Gln Met Ile Ser
        355                 360                 365

Glu Asn Asn Pro Glu Gly Asn Lys Ile Val Arg Asn Leu Ile Asn Asp
    370                 375                 380

Leu Ile Thr Gln Thr Glu Ser Leu Arg Lys Ile Arg Ile Ala Leu Asp
385                 390                 395                 400

Leu Ile Glu Pro Asn Arg Val Ile Gly Asn Val Pro
                405                 410


<210> SEQ ID NO 18
<211> LENGTH: 131
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_02610, COG3755
      uncharacterized protein conserved in bacteria

<400> SEQUENCE: 18
```

Met Cys Arg Lys Ile Ile Phe Ala Leu Thr Ile Ile Ala Ile Ala Phe
1 5 10 15

Gln Ser Met Ala Leu Asn Cys Asn Glu Thr Leu Met Gln Ala Asp Met
20 25 30

Asn Gln Cys Thr Gly Asn Ser Phe Ala Leu Val Lys Glu Lys Leu Glu
35 40 45

Ala Thr Tyr Lys Lys Val Leu Glu Lys Val Glu Lys His Gln Arg Glu
50 55 60

Leu Phe Glu Lys Ser Gln Met Ala Trp Glu Ile Tyr Arg Gly Ser Glu
65 70 75 80

Cys Ala Phe Ala Ala Ser Gly Ala Glu Glu Gly Thr Ala Gln Ser Met
85 90 95

Ile Tyr Ala Asn Cys Leu Gln Gly His Ala Ile Glu Arg Asn Glu Lys
100 105 110

Leu Glu Ser Tyr Leu Thr Cys Pro Glu Gly Asp Leu Leu Cys Pro Phe
115 120 125

Ile Asn Asn
130

<210> SEQ ID NO 19
<211> LENGTH: 205
<212> TYPE: PRT
<213> ORGANISM: Candidatus Liberibacter asiaticus
<220> FEATURE:
<223> OTHER INFORMATION: Candidatus Liberibacter asiaticus strain psy62
outer membrane protein CLIBASIA_02425

<400> SEQUENCE: 19

Met Gln Lys Leu Phe Leu Ala Val Gly Val Ser Ser Leu Ala Leu Ala
1 5 10 15

Ser Phe Cys Ser Ala Gln Ala Ala Asp Pro Val Arg Arg Ala His His
20 25 30

Gly Gly Arg Gly Val Val Pro Thr Ile Ala Thr Asn Arg Tyr Val Pro
35 40 45

Ile Arg His Asp Phe Asn Gly Pro Tyr Ala Gly Leu Ser Ala Leu Tyr
50 55 60

Asn Gly Ser Phe Gly Glu Glu Ala His His Asn Ala Gly Gly Ser Ile
65 70 75 80

Phe Ala Gly Tyr Asn Val Glu Asp Ser Cys Ile Met Tyr Gly Val Glu
85 90 95

Gly Asp Val Arg Tyr Thr Val Pro Val Leu Ala Asp Asn Ile His Ser
100 105 110

Leu His Gly Ile Gly Gly Ser Leu Arg Ile Arg Gly Gly Tyr Glu Val
115 120 125

Ser Asp Ser Leu Leu Leu Tyr Ala Thr Val Gly Pro Asp Val Ala Gln
130 135 140

Lys Tyr Glu Thr Gly Lys Ala Gly Glu Ile Thr Pro Ile Ala Ile Gly
145 150 155 160

Gly Thr Ala Gly Val Gly Val Glu Val Gly Gly Leu Ser Glu Ser Leu
165 170 175

Val Ala Arg Leu Glu Tyr Arg Ala Ser Lys Tyr Ser Lys Val Glu Gly
180 185 190

Phe Tyr Asn Thr Ile Ser Leu Gly Val Gly Met Lys Phe
195 200 205

<210> SEQ ID NO 20
<211> LENGTH: 195
<212> TYPE: PRT
<213> ORGANISM: Candidatus Liberibacter asiaticus
<220> FEATURE:
<223> OTHER INFORMATION: Candidatus Liberibacter asiaticus strain psy62
extracellular solute-binding protein CLIBASIA_02250, COG1840
ABC-type Fe3+ transport system, periplasmic component

<400> SEQUENCE: 20

```
Met Phe Lys Arg Thr Ile Tyr Thr Tyr Leu Leu Leu Leu Cys Gly Phe
 1               5                  10                  15

Thr Glu Ala Phe Ser Thr Glu Asn Thr Thr Lys Tyr Leu Thr Leu Tyr
            20                  25                  30

Thr Asp Gln Asn Gln Ser Val Met Leu Pro Ile Ile His Ser Phe Glu
        35                  40                  45

Glu Arg Thr Gly Val Lys Ile Ser Pro Ile Tyr Thr Ser Ser Ile Gln
    50                  55                  60

Arg Pro Pro Ile Thr Gln Gly Ser Pro Val Asp Val Ile Ile Thr Lys
65                  70                  75                  80

Asp Glu Thr Ser Leu Ala Leu Asn Glu Asp Leu Leu His Lys Leu Pro
                85                  90                  95

Ala His Leu Ile Lys Lys Asn Ser Phe Val Leu Lys Asn Glu Asn Lys
            100                 105                 110

Lys Leu Met Arg Ile Ser Phe Asp Thr Gln Val Leu Ala Tyr Ser Thr
        115                 120                 125

Lys Arg Ile Lys Ile Ala Asp Leu Pro Lys Ser Val Phe Asp Leu Thr
    130                 135                 140

Asn Ala Gln Trp Lys Lys Arg Leu Ser Ile Ala Pro Asn Asn Ile Ser
145                 150                 155                 160

Phe His Arg Leu Leu Asn Thr Met Glu Gln Thr Pro Asn Lys Thr Val
                165                 170                 175

Val Gln Asp Phe Ile Lys Asn Ile Thr Ala Asn Glu Ile Leu Thr Lys
            180                 185                 190

Tyr Lys Arg
        195
```

<210> SEQ ID NO 21
<211> LENGTH: 210
<212> TYPE: PRT
<213> ORGANISM: Candidatus Liberibacter asiaticus
<220> FEATURE:
<223> OTHER INFORMATION: Candidatus Liberibacter asiaticus strain psy62
hypothetical protein CLIBASIA_02145, COG4765
uncharacterized protein conserved in bacteria

<400> SEQUENCE: 21

```
Met Lys Tyr Arg Val Leu Leu Leu Ile Leu Phe Phe Val Phe Ser His
 1               5                  10                  15

Ala Lys Phe Ala Asn Ser Ala Arg Phe Ala Asn Lys Val Ala Glu Phe
            20                  25                  30

Ala Gly Met Asp Lys Ile Thr Gly Arg Val Leu Thr Phe Asp Val Glu
        35                  40                  45

Ile Asn Gln Ser Ala Gln Phe Gly Ser Leu Ile Ile Lys Pro Met Val
    50                  55                  60

Cys Tyr Ser Arg Asp Asp Arg Glu Ala Gln Arg Ile Asp Ala Phe Val
65                  70                  75                  80

Ser Ile Ser Glu Ile Phe Thr Asp Arg Ile Val Arg Ser Ile Phe Ser
                85                  90                  95
```

```
Gly Trp Met Phe Ala Asp Ser Pro Ala Met Asn Ala Ile Asp His Ser
            100                 105                 110

Ile Tyr Asp Ile Trp Leu Met Gln Cys Lys Asp Pro Ile Asn Asp Ser
        115                 120                 125

Ile Ser Asn Ser Glu Ser Ile Ser Lys Lys Ala Leu Ser Glu Tyr Ser
    130                 135                 140

Ser Thr Asp Ile Thr Ser Gln Gly Ser Glu Lys Ser Ser Gly Ser Ser
145                 150                 155                 160

Ser Asn Lys Thr Leu Glu Lys Glu Ser Ser Gln Pro Leu Glu Asn Asn
                165                 170                 175

Leu Ser Met Asp Leu Lys Gly Arg Pro Ile Gln Glu Leu Gly Asn Asn
            180                 185                 190

Leu Ser Asp Ser Gly Leu Asn Glu Gln Asp His Asn Asp Val Gln Ile
        195                 200                 205

Ser Lys
    210
```

<210> SEQ ID NO 22
<211> LENGTH: 294
<212> TYPE: PRT
<213> ORGANISM: Candidatus Liberibacter asiaticus
<220> FEATURE:
<223> OTHER INFORMATION: Candidatus Liberibacter asiaticus strain psy62 periplasmic solute binding protein CLIBASIA_02120, COG0803 ABC-type metal ion transport system, periplasmic component/surface adhesin

<400> SEQUENCE: 22

```
Met Leu Arg Tyr Phe Ile Cys Leu Leu Phe Ser Tyr Ile Pro Met Ser
 1               5                  10                  15

Ala Ser Ala Thr Thr Gln Lys Lys Val Val Leu Ser Ser Phe Ser Ile
            20                  25                  30

Ile Gly Asp Ile Thr Gln Asn Ile Ala Lys Asp Leu Val Thr Val Thr
        35                  40                  45

Thr Leu Val Glu Ala Gly Asn Asp Ser His Ser Tyr Gln Val Thr Ser
    50                  55                  60

Ala Asp Ala Ile Lys Ile Gln Asn Ala Asp Leu Ile Leu Cys Asn Gly
65                  70                  75                  80

Leu His Leu Glu Glu Thr Tyr Met Lys Tyr Phe Thr Asn Leu Lys Lys
                85                  90                  95

Gly Thr Lys Ile Ile Thr Val Thr Asp Gly Ile Asn Pro Ile Gly Val
            100                 105                 110

Ser Glu Asp Thr Ser Val Asp Ser Glu Pro Asn Pro His Ala Trp Met
        115                 120                 125

Ser Leu Thr Asn Ala Met Ile Tyr Ile Glu Asn Ile Arg Lys Ala Leu
    130                 135                 140

Thr Ala Leu Asp Pro Ser Asn Ala Lys Lys Tyr Glu Leu Asn Ala Arg
145                 150                 155                 160

Glu Tyr Ser Glu Lys Ile Arg Asn Ser Ile Leu Pro Leu Lys Thr Arg
                165                 170                 175

Ile Glu Lys Val Asp Pro Glu Lys Arg Trp Phe Val Thr Ser Glu Gly
            180                 185                 190

Cys Leu Val Tyr Leu Ala Glu Asp Phe Gly Phe Lys Ser Leu Tyr Leu
        195                 200                 205

Trp Pro Ile Asn Ser Asp Ser Glu Arg Ser Pro Ser Met Met Arg His
    210                 215                 220
```

```
Ala Ile Asn Gln Met Arg Ser His Lys Ile Lys Phe Ile Phe Ser Glu
225                 230                 235                 240

Ser Thr Asn Ser Asp Gln Pro Ala Lys Gln Val Ala Tyr Glu Thr Asn
                245                 250                 255

Ala Ser Tyr Gly Gly Val Leu Tyr Val Asp Ser Leu Ser Lys Pro Asp
            260                 265                 270

Gly Pro Ala Pro Thr Tyr Leu Asp Leu Leu Arg Phe Ser Leu Thr Lys
        275                 280                 285

Ile Val Asp Thr Leu Phe
    290


<210> SEQ ID NO 23
<211> LENGTH: 96
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_04025

<400> SEQUENCE: 23

Met Thr Ile Ser Lys Asn Gln Ala Ile Leu Phe Phe Ile Thr Gly Met
 1               5                  10                  15

Ile Leu Ser Ser Cys Gly Asp Thr Leu Ser Asp Ser Lys Gln His Asn
            20                  25                  30

Lys Ile Asn Asn Thr Lys Asn His Leu Asp Leu Leu Phe Pro Ile Asp
        35                  40                  45

Asp Ser His Asn Gln Lys Pro Thr Glu Lys Lys Pro Asn Thr Ser Ser
    50                  55                  60

Ile Lys Ile Lys Asn Asn Ile Ile Glu Pro Gln Pro Gly Pro Ser Arg
65                  70                  75                  80

Trp Glu Gly Gly Trp Asn Gly Glu Arg Tyr Val Arg Glu Trp Glu Arg
                85                  90                  95


<210> SEQ ID NO 24
<211> LENGTH: 159
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_04040

<400> SEQUENCE: 24

Met Lys Arg Leu Lys Tyr Gln Ile Ile Leu Leu Ser Leu Leu Ser Thr
 1               5                  10                  15

Thr Met Ala Ser Cys Gly Gln Ala Asp Pro Val Ala Pro Pro Pro Pro
            20                  25                  30

Gln Thr Leu Ala Glu Arg Gly Lys Ala Leu Leu Asp Glu Ala Thr Gln
        35                  40                  45

Lys Ala Ala Glu Lys Ala Ala Glu Ala Ala Arg Lys Ala Ala Glu Gln
    50                  55                  60

Ala Ala Glu Ala Ala Lys Lys Ala Ala Glu Lys Ile Ile His Lys Asp
65                  70                  75                  80

Lys Lys Lys Pro Lys Glu Asn Gln Glu Val Asn Glu Val Pro Val Ala
                85                  90                  95

Ala Asn Ile Glu Pro Glu Ser Gln Glu Thr Gln Gln Gln Val Ile Asn
            100                 105                 110

Lys Thr Thr Thr Ser Gln Thr Asp Ala Glu Lys Thr Pro Asn Glu Lys
        115                 120                 125
```

```
Arg Gln Gly Thr Thr Asp Gly Ile Asn Asn Gln Ser Asn Ala Thr Asn
    130                 135                 140

Asp Pro Ser Ser Lys Asp Lys Ile Ala Glu Asn Thr Lys Glu Asp
145                 150                 155


<210> SEQ ID NO 25
<211> LENGTH: 276
<212> TYPE: PRT
<213> ORGANISM: Candidatus Liberibacter asiaticus
<220> FEATURE:
<223> OTHER INFORMATION: Candidatus Liberibacter asiaticus strain psy62
      rare lipoprotein A CLIBASIA_04170, COG0797 lipoprotein

<400> SEQUENCE: 25

Met Lys Arg Phe Ser Cys Asp Cys Leu Leu Lys Gly Ser Val Val Cys
 1               5                  10                  15

Val Val Val Leu Gly Met Ser Ser Cys Phe Phe Ser Ser Thr Tyr Lys
            20                  25                  30

Asp Asp Lys Leu Glu Tyr Phe Pro Glu Ser Met Tyr Gly Val Thr Ala
        35                  40                  45

Ser Asp Arg Ile Val Ser Gly Lys Arg Val Pro Arg Gly Gly Gly Arg
    50                  55                  60

Tyr Phe Leu Gly Lys Pro Tyr Gln Ile Met Gly Arg Trp Tyr Val Pro
65                  70                  75                  80

Arg Gln Tyr Thr Ala Tyr Ala Ala Val Gly Met Ala Ser Trp Tyr Gly
                85                  90                  95

Lys Ala Phe His Gly Arg Leu Thr Ala Asn Gly Glu Val Tyr Gly Thr
            100                 105                 110

Glu Tyr Ile Thr Ala Ala His Pro Thr Leu Pro Leu Pro Ser Tyr Val
        115                 120                 125

Arg Val Thr Asn Met Glu Asn Gly Ile Ser Leu Val Val Arg Val Asn
    130                 135                 140

Asp Arg Gly Pro Tyr His Ser Asn Arg Leu Ile Asp Leu Ser Asn Ala
145                 150                 155                 160

Ala Ala Lys Ile Leu Arg Val Glu Glu Arg Gly Val Ser Lys Val His
                165                 170                 175

Val Glu Tyr Leu Gly Met Ala Leu Leu Asn Gly Met Asp Gln Glu Tyr
            180                 185                 190

Leu Arg Ser Thr Val Met Val Asn Ser Ala Thr Val Leu Pro Leu Gly
        195                 200                 205

Cys Gln Tyr Arg Glu Glu Ile Val Val Ile Pro Tyr Leu Leu Thr Arg
    210                 215                 220

Ser Arg Thr Val His Leu Asn Asn Cys Asp Asp Asp Ser Leu Gln Lys
225                 230                 235                 240

Gln Arg Glu Ile Ser Leu Arg Glu Arg Lys Lys Ser Asn Leu Ile Pro
                245                 250                 255

Leu Pro Asn Gly Tyr Ser Pro Pro Arg Lys Met Gly Lys Ile Pro Ile
            260                 265                 270

Pro Ser Arg Phe
        275


<210> SEQ ID NO 26
<211> LENGTH: 304
<212> TYPE: PRT
<213> ORGANISM: Candidatus Liberibacter asiaticus
<220> FEATURE:
<223> OTHER INFORMATION: Candidatus Liberibacter asiaticus strain psy62
```

hypothetical protein CLIBASIA_04520

<400> SEQUENCE: 26

```
Met Ile Arg Lys Tyr Val Leu Ala Leu Val Phe Phe Leu Val Pro Cys
 1              5                   10                  15

Thr Ala Ser Val Ala Gln Lys Val Arg Leu Val Ser Trp Asn Ile Asn
            20                  25                  30

Thr Leu Ser Glu Gln Glu Gly Val Ser Leu Trp Lys Asn Ser Val Lys
        35                  40                  45

Arg Thr Thr Ser Asp Tyr Thr Leu Leu Arg Gln Tyr Ala Lys Asn Leu
    50                  55                  60

Asp Ala Asp Ile Val Phe Leu Gln Glu Met Gly Ser Tyr Asn Ala Val
65                  70                  75                  80

Ala Lys Val Phe Pro Lys Asn Thr Trp Cys Ile Phe Tyr Ser Thr Glu
                85                  90                  95

Arg Leu Ile Asn His Ser Lys Arg Asp Ser Asn Asn Asp Ile His Thr
            100                 105                 110

Ala Ile Ala Val Arg Lys Lys Asn Val Arg Val Leu Gln Gln Ser Tyr
        115                 120                 125

Pro Leu Leu Gly Ala Lys Asp Ser Phe Ser Arg Ala Gly Asn Arg Arg
    130                 135                 140

Ala Val Glu Leu Leu Val Glu Ile Asn Gly Lys Lys Ile Trp Val Leu
145                 150                 155                 160

Asp Ile His Leu Lys Ser Phe Cys Phe Leu Asp Ser Leu Glu Asn Thr
                165                 170                 175

Tyr Ser Pro Ser Cys Ser Leu Leu Ser Gln Gln Ala Gln Trp Leu Lys
            180                 185                 190

Asp Trp Ile Thr Gln Lys Lys Glu Ser Leu Val Pro Phe Val Ile Ala
        195                 200                 205

Gly Asp Phe Asn Arg Lys Ile Asn Tyr Leu Gly Asn Asn Asp Asp Phe
    210                 215                 220

Trp Lys Thr Ile Asp Pro Asn Asp Ser Leu Ile Arg Phe Pro Lys Glu
225                 230                 235                 240

Lys Asp Ser Arg Cys Asn Ala Asn Lys Asn Leu Arg Asn Lys Ile Pro
                245                 250                 255

Ile Asp Tyr Phe Val Met Asp Gln Asn Ala Tyr Lys Phe Leu Ile Gln
            260                 265                 270

Glu Ser Phe Ser Glu Ile Leu Tyr Asn Glu Asp Asp Ile Lys Ser Arg
        275                 280                 285

Gly Lys Arg Leu Ser Asp His Cys Pro Ile Ser Ile Asp Tyr Asp Phe
    290                 295                 300
```

<210> SEQ ID NO 27
<211> LENGTH: 116
<212> TYPE: PRT
<213> ORGANISM: Candidatus Liberibacter asiaticus
<220> FEATURE:
<223> OTHER INFORMATION: Candidatus Liberibacter asiaticus strain psy62
hypothetical protein CLIBASIA_04580

<400> SEQUENCE: 27

```
Met Phe Trp Ile Ala Lys Lys Phe Phe Trp Ile Ser Val Leu Leu Ile
 1              5                   10                  15

Val Leu Ser Asn Val Tyr Ala Gln Pro Phe Leu Glu Glu Thr Glu Lys
            20                  25                  30

Gly Lys Lys Thr Glu Ile Thr Asp Phe Met Thr Ala Thr Ser Gly Thr
```

```
        35                  40                  45

Val Gly Tyr Ala Ser Asn Leu Cys Asn Ala Lys Pro Glu Ile Cys Leu
    50                  55                  60

Leu Trp Lys Lys Ile Met Arg Asn Val Lys Arg His Thr Leu Asn Gly
65                  70                  75                  80

Ala Lys Ile Val Tyr Gly Phe Ala Lys Ser Ala Leu Glu Lys Asn Glu
                85                  90                  95

Arg Glu Ser Val Ala Ile His Ser Lys Asn Glu Tyr Pro Pro Pro Leu
            100                 105                 110

Pro Ser His His
        115


<210> SEQ ID NO 28
<211> LENGTH: 185
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_05115

<400> SEQUENCE: 28

Met Phe Leu Asn Val Leu Lys Asp Phe Phe Val Pro Arg Ile Arg Phe
 1               5                  10                  15

Leu Ile Val Leu Met Val Ser Ser Val Ser Ala Gly Tyr Ala Asn Ala
            20                  25                  30

Ser Gln Pro Glu Pro Thr Leu Arg Asn Gln Phe Ser Arg Trp Ser Val
        35                  40                  45

Tyr Val Tyr Pro Asp Leu Asn Lys Lys Leu Cys Phe Ser Leu Ser Val
    50                  55                  60

Pro Val Thr Val Glu Pro Leu Glu Gly Val Arg His Gly Val Asn Phe
65                  70                  75                  80

Phe Ile Ile Ser Leu Lys Lys Glu Glu Asn Ser Ala Tyr Val Ser Glu
                85                  90                  95

Leu Val Met Asp Tyr Pro Leu Asp Glu Glu Glu Met Val Ser Leu Glu
            100                 105                 110

Val Lys Gly Lys Asn Ala Ser Gly Thr Ile Phe Lys Met Lys Ser Tyr
        115                 120                 125

Asn Asn Arg Ala Ala Phe Glu Lys Arg Ser Gln Asp Thr Val Leu Ile
    130                 135                 140

Glu Glu Met Lys Arg Gly Lys Glu Leu Val Val Ser Ala Lys Ser Lys
145                 150                 155                 160

Arg Gly Thr Asn Thr Arg Tyr Ile Tyr Ser Leu Ile Gly Leu Ser Asp
                165                 170                 175

Ser Leu Ala Asp Ile Arg Lys Cys Asn
            180                 185


<210> SEQ ID NO 29
<211> LENGTH: 154
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_05315

<400> SEQUENCE: 29

Met Arg Lys Asn Leu Leu Thr Ser Thr Ser Ser Leu Met Phe Phe Phe
 1               5                  10                  15

Leu Ser Ser Gly Tyr Ala Leu Ser Gly Ser Ser Phe Gly Cys Cys Gly
```

```
            20                  25                  30

Glu Phe Lys Lys Lys Ala Ser Ser Pro Arg Ile His Met Arg Pro Phe
        35                  40                  45

Thr Lys Ser Ser Pro Tyr Asn Asn Ser Val Ser Asn Thr Val Asn Asn
    50                  55                  60

Thr Pro Arg Val Pro Asp Val Ser Glu Met Asn Ser Ser Arg Gly Ser
65                  70                  75                  80

Ala Pro Gln Ser His Val Asn Val Ser Ser Pro His Tyr Lys His Glu
                85                  90                  95

Tyr Ser Ser Ser Ser Ala Ser Ser Ser Thr His Ala Ser Pro Pro Pro
            100                 105                 110

His Phe Glu Gln Lys His Ile Ser Arg Thr Arg Ile Asp Ser Ser Pro
        115                 120                 125

Pro Pro Gly His Ile Asp Pro His Pro Asp His Ile Arg Asn Thr Leu
    130                 135                 140

Ala Leu His Arg Lys Met Leu Glu Gln Ser
145                 150


<210> SEQ ID NO 30
<211> LENGTH: 208
<212> TYPE: PRT
<213> ORGANISM: Candidatus Liberibacter asiaticus
<220> FEATURE:
<223> OTHER INFORMATION: Candidatus Liberibacter asiaticus strain psy62
      putative ABC transporter protein CLIBASIA_00100, COG3218 ABC-type
      uncharacterized transport system, auxiliary component

<400> SEQUENCE: 30

Met Asp Lys Lys Leu Asn Lys Ile Ile Lys Lys Lys Ile Ile Ser Cys
 1               5                  10                  15

Ser Leu Ala Val Leu Leu Cys Thr Ser Leu Ser Ser Cys Phe Phe His
            20                  25                  30

Asn Asn Pro Val Asn Ile Tyr Asp Leu Thr Glu Ser Thr Lys Tyr Asp
        35                  40                  45

Glu Ser Val Gln Arg His Ile Gln Leu Ile Ile Thr Glu Pro Ile Thr
    50                  55                  60

Glu Lys Ile Leu Asn Ser Glu Asp Ile Ile Val Arg Ser Ser Pro Ile
65                  70                  75                  80

Glu Ile Gln Tyr Leu Ile Gly Ser Gln Trp Ser Asp Lys Leu Pro Arg
                85                  90                  95

Met Ile Gln Leu Lys Leu Ile Ala Asn Phe Glu Asn Asn Gly Lys Ile
            100                 105                 110

Ser Thr Val Val Lys Pro Asn Gln Gly Ile Tyr Ala Asp Tyr Gln Ile
        115                 120                 125

Ile Ser Ala Ile Arg Ser Phe Glu Ile Asn Ile Asp Arg His Cys Ala
    130                 135                 140

Ile Ile Thr Met Ser Leu Lys Ile Ile Asn Ala His Asp Asn Ser Leu
145                 150                 155                 160

Val Gly Gln Lys Val Phe His Val Glu Glu Lys Leu Glu Lys Asp Asn
                165                 170                 175

Lys Leu His Phe Ile Gln Ser Leu Asn Arg Ala Phe Ser Arg Ile Ser
            180                 185                 190

Ser Glu Ile Ile Asp Trp Thr Leu Ser Ser Leu Pro Leu Ser Asp Asn
        195                 200                 205


<210> SEQ ID NO 31
```

<211> LENGTH: 396
<212> TYPE: PRT
<213> ORGANISM: Candidatus Liberibacter asiaticus
<220> FEATURE:
<223> OTHER INFORMATION: Candidatus Liberibacter asiaticus strain psy62
      chemotaxis protein CLIBASIA_02075

<400> SEQUENCE: 31

```
Met Asn Gln Lys Tyr Leu Ile Cys Thr Met Met Val Ala Met Asp Val
 1               5                  10                  15

Phe Phe Ser Phe Ala Thr Asp Gln Asp Leu Val Arg Thr Ile Val Pro
            20                  25                  30

Tyr Gln Cys Val Arg Ser Leu Gln Arg Ala Leu Asp Glu Ala Met Arg
        35                  40                  45

Gly Asp Ile Ser Leu Gln Lys Lys Ile Pro Asp Ile Val Lys Glu Thr
    50                  55                  60

Gly Val Gln Leu Arg Ala Thr His Met Asp Val Phe Val Asp Asn Arg
65                  70                  75                  80

Asn Ile Asp Ala Val Trp Ile Tyr Thr Ile Ile Ser Gln Asp Leu Ser
                85                  90                  95

Val Val Asp Asp Leu Ile Ala Lys Asp Thr Lys Gly Tyr Phe Asp Ile
            100                 105                 110

Ala Ile Val Tyr Ala Leu Lys Lys Tyr Phe Ser Gly Gln Leu Glu Glu
        115                 120                 125

Ser Ser Lys Glu Leu Ser Lys Ile Lys Asp Lys Asp Asn Thr Arg Gly
    130                 135                 140

Ile Val Pro Tyr Leu His Leu Leu Ile Gly Arg Ala Met Met Pro Phe
145                 150                 155                 160

Ser Ser Gln Gln Ala Val His Phe Phe Asp Tyr Val Arg Leu Thr Ser
                165                 170                 175

Pro Gly Thr Phe Leu Glu Glu Ile Ala Leu Arg Asn Leu Leu Glu Ile
            180                 185                 190

Thr Gln Asn Glu Val Gly Glu Arg Ala Phe Gly Tyr Ile Arg Ala Tyr
        195                 200                 205

Val Thr Gln Phe His His Ser Ile Tyr Lys Asp His Phe Ile Ser Val
    210                 215                 220

Leu Leu Arg Phe Phe Leu His Gly Gln Leu Lys Leu Pro Asp Glu Asp
225                 230                 235                 240

Ile Val Phe Thr Ile Ser Phe Phe Ser Leu Glu Glu Gln Arg Ala Ile
                245                 250                 255

Tyr Leu Lys Ile Ala Gln Asn Ser Val Ile Ser Gly Lys Arg Lys Ile
            260                 265                 270

Gly Phe Leu Ala Ile Lys Gln Leu Lys Arg Ile Ile Asp Arg Leu Asp
        275                 280                 285

Tyr Lys Asp Leu Ala Thr Ile Gln Leu Tyr Glu Asn Ile Leu Asn Ile
    290                 295                 300

Pro Phe Val Asp Ile Met Ser Leu Gln Arg Ser Thr Cys Asn Ile Pro
305                 310                 315                 320

Tyr Tyr Ser Leu Met Glu Gln Asp Arg Tyr Leu Lys Lys Ala Ser Glu
                325                 330                 335

Ile Ile Met Ser Glu Ile Gly Lys Ser Leu Ile Asp Ile Asp Phe Glu
            340                 345                 350

His Ile Gln Lys Asp Leu Leu Leu Asp Lys Lys Glu Pro Arg His Thr
        355                 360                 365

Asn Val Ser Met Gly Ile Glu Ser Phe Ile Lys Lys Asn Arg Ser Gln
```

```
    370                 375                 380

Ile Glu Ser Ile Asp Val Leu Leu Ala Glu Ala Arg
385                 390                 395


<210> SEQ ID NO 32
<211> LENGTH: 60
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_03120

<400> SEQUENCE: 32

Met Ala Arg Thr Gln Ile Ala Leu Ala Leu Ser Phe Phe Met Ile Thr
 1               5                  10                  15

His Ser Tyr Tyr Ala Phe Ser Gln Asp Glu Ile Lys Lys Asn Asn Pro
            20                  25                  30

Thr Leu Glu Lys Lys Pro Ile Val Leu Met Lys His Glu Ile Gln Glu
        35                  40                  45

Lys Lys Thr Leu Ala Ala Phe Thr Ser Phe Ala Ser
    50                  55                  60


<210> SEQ ID NO 33
<211> LENGTH: 195
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_04560

<400> SEQUENCE: 33

Met Lys Ser Lys Asn Ile Leu Ile Val Ser Thr Leu Val Ile Cys Val
 1               5                  10                  15

Leu Ser Ile Ser Ser Cys Asp Leu Gly Asp Ser Ile Ala Lys Lys Arg
            20                  25                  30

Asn Thr Ile Gly Asn Thr Ile Lys Lys Ser Ile Asn Arg Val Ile Gln
        35                  40                  45

Glu Asn Asn Lys Pro Arg Asn Met Thr Ile Phe Lys Thr Glu Val Lys
    50                  55                  60

Arg Asp Ile Arg Arg Ala Ser Arg Leu Ser Leu Glu Glu Lys Ser Lys
65                  70                  75                  80

Asn Ala Asp Lys Pro Thr Val Ile Glu Asn Gln Ala Asp Asn Ile Asn
                85                  90                  95

Ile Glu Val Glu Val Ala Thr Asn Leu Asn Pro Asn His Gln Ala Ser
            100                 105                 110

Glu Ile Asp Ile Ala Ile Glu Asn Leu Pro Asp Leu Lys Ser Asn His
        115                 120                 125

Gln Ala Ser Glu Ile Asp Ile Ala Ile Glu Asn Leu Pro Asp Leu Lys
    130                 135                 140

Ser Asn His Gln Ala Ser Glu Ile Asp Ile Ala Ile Glu Asn Leu Pro
145                 150                 155                 160

Asp His Gln Val Asp Arg Asn His Thr Leu Ser Asn Leu Arg Gly Ala
                165                 170                 175

Cys Tyr Gln Pro Ser Leu Val Ser Asn Ser Ser Leu Lys Leu Trp Asp
            180                 185                 190

Val Ala Phe
        195
```

-continued

```
<210> SEQ ID NO 34
<211> LENGTH: 68
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_05640

<400> SEQUENCE: 34

Met Thr Ile Lys Lys Val Leu Ile Ala Ser Thr Leu Leu Ser Leu Cys
 1               5                  10                  15

Gly Cys Gly Leu Ala Asp Glu Pro Lys Lys Leu Asn Pro Asp Gln Leu
            20                  25                  30

Cys Asp Ala Val Cys Arg Leu Thr Leu Glu Glu Gln Lys Glu Leu Gln
        35                  40                  45

Thr Lys Val Asn Gln Arg Tyr Glu Glu His Leu Thr Lys Gly Ala Lys
    50                  55                  60

Leu Ser Ser Asp
65


<210> SEQ ID NO 35
<211> LENGTH: 85
<212> TYPE: PRT
<213> ORGANISM: Candidatus Liberibacter asiaticus
<220> FEATURE:
<223> OTHER INFORMATION: Candidatus Liberibacter asiaticus strain psy62
      hypothetical protein CLIBASIA_05320

<400> SEQUENCE: 35

Met Ser Lys Phe Val Val Arg Ile Met Phe Leu Leu Ser Ala Ile Ser
 1               5                  10                  15

Ser Asn Pro Ile Leu Ala Ala Asn Glu His Ser Ser Val Ser Glu Gln
            20                  25                  30

Lys Arg Lys Glu Thr Thr Val Gly Phe Ile Ser Arg Leu Val Asn Lys
        35                  40                  45

Arg Pro Val Ala Asn Lys Arg Cys Pro Asn Ala Thr Lys Gln Thr Pro
    50                  55                  60

Pro Asp His Gly Ser Lys Tyr Asp Thr Arg Glu Val Leu Met Leu Phe
65                  70                  75                  80

Gly Gly Leu Asn Asn
                85
```

IDENTIFICATION OF SECRETED PROTEINS AS DETECTION MARKERS FOR CITRUS DISEASE

CROSS-REFERENCES TO RELATED APPLICATIONS

This application claims priority to U.S. Provisional Application No. 61/615,760, filed on Mar. 26, 2012, the disclosure of which is hereby incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-2112-1.TXT, created on May 23, 2013, 94,208 bytes, machine format IBM-PC, MS-Windows operating system, is hereby incorporated by reference in its entirety for all purposes.

BACKGROUND OF THE INVENTION

Citrus production is one of the most important agricultural economic activities in the United States and around the world. According to the Food and Agricultural Organization (FAO) of the U.N., approximately 47,170 tons of citrus fruits such as oranges, lemons, grapefruits, etc., were produced in 2011, corresponding to US$2.3 billion from sales of fresh fruits and juices around worldwide (FAOSTAT). However, the citrus industry has been experiencing a big threat from phloem-colonizing and insect-transmitted bacterial diseases including Citrus Stubborn Disease (CSD) and Huanglongbing (HLB, also known as citrus greening). Diagnosis of these diseases has been very challenging because of the low titer and uneven distribution of the pathogens in the citrus tree.

The causative bacteria *Candidatus Liberibacter* (for HLB) and *Spiroplasma citri* (for CSD) reside exclusively in the phloem of infected trees once they are introduced by the phloem-feeding insect vectors or by grafting. So far, CSD or HLB resistant varieties of citrus have not been found.

The most commonly used pathogen detection methods are PCR based, which requires the presence of bacterial cells or DNA on the tested sample for positive diagnosis. This is been problematic because the low titer and variable distribution of the pathogen within infected trees. Both *S. citri* and *Ca. Liberibacter* cells exhibit extremely uneven distributions in infected trees. Very often, the pathogen cells cannot be detected even in symptomatic branches or leaves. Moreover, nucleic acid-based assays require sample preparations, which can be complex, costly and time consuming, especially when numerous samples have to be tested for one tree. So far, the ability to process thousands of samples necessary to track an epidemic using nucleic acid-based methods remains man-power and cost challenging.

Bacteria pathogens secrete numerous proteins to the environment and some of these secreted proteins are essential virulence factors functioning in plant cells. Genes encoding these specialized pathogenesis-related protein secretion apparatus are present in the host plant, but absent from *S. citri* and *Ca. Liberibacter*. Bacterial pathogens are injected into plant tissues, i.e., the phloem, by their corresponding insect vectors at the initial stage of infection; therefore, proteins secreted from the general secretion system are readily delivered inside the host cells. This is consistent with the observation that the pathogen cells are often absent from symptomatic tissues. While not being bound by any particular theory, it is believed that the presence of secreted proteins are responsible for the symptom development. Importantly, there are no curative methods once the trees are infected. The success of disease management is largely dependent on early pathogen detection.

BRIEF SUMMARY OF THE INVENTION

One aspect presented herein is a method of detecting citrus stubborn disease (CSD) in a citrus plant. The method includes detecting the presence or absence of a secreted protein from *Spiroplasma citri* in a sample from the plant, whereby the presence of the secreted protein indicates that the plant has citrus stubborn disease. In some embodiments, the sample or sap is not subjected to protein separation or other methods of isolating, extracting or purifying proteins in the sample prior to the detecting step.

In some embodiments, the secreted protein for detecting CSD is CAK98563, or is substantially identical to the protein CAK98563. The CAK98563 protein (SEQ ID NO:1), also referred to as ScCCPP1, is predicted to be a transmembrane lipoprotein. In some embodiments, the secreted protein is CAK99824, or is substantially identical to the protein CAK99824. The CAK99824 protein (SEQ ID NO:2) is predicted to be a transmembrane lipoprotein. In some embodiments, the secreted protein is identical or substantially identical to a protein listed in Table 1.

Another aspect presented herein is a method of detecting citrus greening disease (Huanglongbing or HLB) in a citrus plant. The method includes detecting the presence or absence of a secreted protein from *Candidatus Liberibacter* asiaticus in a sample from the plant, whereby the presence of the secreted protein indicates that the plant has HLB. In some embodiments, the sample or sap is not subjected to protein separation or other methods of isolating, extracting or purifying proteins in the sample prior to the detecting step.

In some embodiments, the secreted protein for detecting HLB is identical or substantially identical to a protein listed in Table 2.

In some embodiments, the citrus plant is not artificially infected or graft-inoculated with a bacterial pathogen.

In some embodiments, the secreted protein is detected by detecting the specific binding of an antibody to the secreted protein. In some instances, the antibody binds to the secreted protein CAK98563, or to the secreted protein substantially identical to the protein CAK98563. In some instances, the antibody binds to the secreted protein CAK99824, or to the secreted protein substantially identical to the protein CAK99824. In some instances, the antibody binds to a secreted protein that is identical or substantially identical to a protein listed in Table 1. In other instances, the antibody binds to a secreted protein that is identical or substantially identical to a protein listed in Table 2.

In some embodiments, if a plant is determined to have CSD (*Spiroplasma citri*) or HLB (*Candidatus Liberibacter* asiaticus), the infected plant is removed and or destroyed.

Another aspect presented herein is a kit for detecting citrus stubborn disease. The kit contains one or more reagent specific for a secreted protein from *Spiroplasma citri*. In some instances, the reagent is an antibody. In some embodiments, at least one reagent of the kit is an antibody that specifically binds to the secreted protein CAK98563, or to the secreted protein substantially identical to the protein CAK98563. In some embodiments, at least one reagent of the kit is an antibody that specifically binds to the secreted protein CAK99824, or to the secreted protein substantially identical to the protein CAK99824. In some embodiments, at least one reagent of the kit is an antibody that specifically binds to a secreted protein that is identical or substantially identical to a protein listed in Table 1.

Another aspect presented herein is a kit for detecting citrus greening disease. The kit contains one or more reagent specific for a secreted protein from *Candidatus Liberibacter* asiaticus. In some instances, the reagent is an antibody. In some embodiments, at least one reagent of the kit is an antibody that specifically binds to a secreted protein that is identical or substantially identical to a protein listed in Table 2.

In some embodiments, the antibody of the kit for CSD or HLB is labeled. In some instances, the antibody has a detectable label (e.g., fluoroscent dye, enzyme, biotin, etc.).

In some embodiments, the antibody of the kit for CSD or HLB is linked to a solid support. Non-limiting examples of a solid support include the surface of an ELISA plate, a glass slide, a coated plate, a bead such as a silica, plastic or derivatized plastic, paramagnetic or non-magnetic metal bead, a polymeric gel or matrix, or a filter, such as a nylon or nitrocellulose.

In some embodiments, the kit for CSD comprises more than one antibody that specifically binds to any one of the proteins (or substantially identical variants thereof) described in Table 1, wherein a first antibody that binds the protein of interest is linked to a solid support and a second antibody that binds the protein of interest is labeled with a detectable moiety.

In some embodiments, the kit for HLB comprises more than one antibody that specifically binds to any one of the proteins (or substantially identical variants thereof) described in Table 2, wherein a first antibody that binds the protein of interest is linked to a solid support and a second antibody that binds the protein of interest is labeled with a detectable moiety.

Also provided are antibodies (optionally isolated) that specifically bind to secreted proteins as described herein. In some embodiments, the antibody specifically binds a secreted protein that is identical or substantially identical to a protein listed in Table 1. In some embodiments, the antibody that specifically binds to the secreted protein (i.e., SEQ ID NO:1) CAK98563, or to the secreted protein substantially identical to the protein (i.e., SEQ ID NO:1) CAK98563. In some embodiments, the antibody that specifically binds to the secreted protein CAK99824 (i.e., SEQ ID NO:2), or to the secreted protein substantially identical to the protein (i.e., SEQ ID NO:2) CAK99824. In some embodiments, the antibody specifically binds a secreted protein that is identical or substantially identical to a protein listed in Table 2. In some embodiments, the antibody is detectably-labeled. In some embodiments, the antibody linked to a solid support.

BRIEF DESCRIPTION OF THE DRAWINGS

FIG. 1 shows Western blot analysis of ScCCPP1 protein CAK98563 and spiralin protein in *S. citri* cells alone and *S. citri* cells in phloem extracts.

FIG. 4 illustrates one embodiment of the method described herein.

DETAILED DESCRIPTION OF THE INVENTION

I. Introduction

Figure 1A:
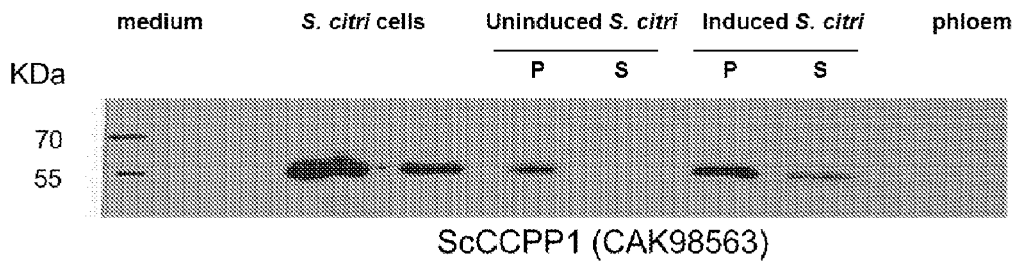
FIG. 1A shows that the secreted protein is present in *S. citri* cells alone and *S. citri* cells in phloem extracts.

Methods for serologically diagnosing CSD using *S. citri*-specific secreted protein or HLB using *C. liberibacter*-specific secreted protein in a sample are provided. Bacterial pathogens secrete effector proteins into their hosts during infection. These effectors are usually unique for specific pathogen species or even subspecies. It has been discovered that secreted effector proteins can be used as detection markers for diagnosis of bacterial diseases. Antibodies generated to specifically recognize suitable effector proteins can be used to develop serological detection methods such as enzyme-linked immunosorbent assay (ELISA) and imprint detection. The method described herein is particularly efficient for detecting disease in trees where detection of pathogens using nucleic acid-based methods, such as polymerase chain reaction, is challenging due to the uneven distribution of the pathogens in the infected trees. Furthermore, many bacterial pathogens reside in plant transportation systems, i.e. xylem and phloem; therefore, effectors secreted from the pathogens can be dispersed through nutrient and water transportation.

The method described below is advantageous over other detection methods such as nucleic acid-based detections in two ways: 1) it can overcome the problem of erratic distribution and low titer of the pathogens in the host plant; 2) antibody-based serological detection methods allow rapid and economical processing of a large amount of samples in applications like field surveys.

II. Definitions

As used herein and in the appended claims, the singular forms "a," "and," and "the" include plural referents unless the context clearly dictates otherwise. Thus, for example, reference to "a plant" includes a plurality of such plants and reference to "the tree" includes reference to one or more trees known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94% 95%, 96%, 97%, 98%, or 99%, compared to a reference sequence using the programs described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is the only natural codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, *Proteins* (1984)).

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a molecule (e.g., antibody) with defined binding characteristics (e.g., a polypeptide with a known binding specificity), so as to allow the presence of the molecule (and therefore its binding target) to be readily detectable.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the methods of the invention includes angiosperms (monocotyledonous and dicotyledonous plants), gymnosperms, ferns, bryophytes, and multicellular and unicellular algae. It includes plants of a variety of ploidy levels, including aneuploid, polyploid, diploid, haploid, and hemizygous. In some embodiments, the secreted protein is detected in a biological sample from a citrus plant. For example, the biological sample can comprise fluid or sap from bark, fruit, a leaf, a leaf petriole, a branch, a twig, or other tissue from an infected or control plant. In some embodiments, the citrus plant is an orange tree, a lemon tree, a lime tree, or a grapefruit tree. In one embodiment, the citrus plant is a navel orange, Valencia orange, sweet orange, mandarin orange, or sour orange. In one embodiment, the citrus plant is a lemon tree. In one embodiment, the citrus plant is a lime tree. In some embodiments, the plant is a relative of a citrus plant, such as orange jasmine, limeberry, and trifoliate orange.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*.

III. Detailed Description of Embodiments

Herein is provided a serological detection method for monitoring the effectors secreted from the pathogens into the phloem, wherein the pathogen secreted proteins are markers for citrus stubborn disease. The method includes using an antibody to detect a secreted protein of the bacterial pathogen *Spiroplasma citri*. Because the causal pathogens *Candidatus Liberibacter* and *Spiroplasma citri* reside in the phloem of infected trees, secreted proteins are dispersed throughout the tree along with the transportation flow in the host vascular system. Therefore, although the pathogens cells have a restricted and sporadic distribution pattern, the pathogen proteins are not restricted to the infection sites. This allows for robust detection and overcomes the difficulty from the uneven distribution of the pathogen cells in infected trees. Furthermore, direct detection of pathogen-associated patterns are more reliable and highly selectivity, especially compared to detections of host changes, which may not be specific to a particular disease.

Accordingly, in some embodiments, methods of detecting citrus stubborn disease or citrus greening disease, or the presence of the causative agents, *Spiroplasma citri*, and *Candidatus Liberibacter* asiaticus, respectively, by detecting one or more secreted protein from the causative agents are provided.

Surprisingly, it has been discovered that the presence of citrus stubborn disease can be detected by detecting a secreted protein as described herein in untreated (unpurified) sap from infected citrus, even trees that are naturally infected and thus have a lower titer of bacteria than an artificially-infected tree. This is particularly surprising as spiralin, a highly-expressed protein from *Spiroplasma citri* cannot be detected from unpurified sap (see, e.g., FIG. 3B). Accordingly, in some embodiments, the sample of the methods includes fluid of the vascular system (e.g., sap) from a plant located in the field. In some embodiments, a sample is obtained from a plant and is not processed to separate, isolated or purify the secreted protein of interest from other proteins of the sample. For example, the sample is not subjected to extraction, electrophoresis (e.g., polyacrylamide gel electrophoresis, isoelectric focusing electrophoresis), chromatography (e.g., size chromatography, affinity chromatography), or magnetic bead separation prior to detecting the presence of the secreted protein of interest.

Further, in some embodiments, the plant that does not comprise grafting-inoculated citrus tissue or other artificially-inoculated tissue. In some instances, the sample is from phloem-rich tissue.

The methods described herein can be used to detect a secreted protein that is not abundant on *S. citri* cells. For instance, the secreted protein can be present at a lower level than spiralin which has been shown to be the most abundant protein at the membrane of *S. citri* cells (see, Duret et al., *Appl. Environ. Microbiol.,* 69:6225-6234 (2003)). Detection of the presence of the secreted protein in a plant sample indicates that the plant has citrus stubborn disease.

In some embodiments, the secreted protein is detected with an antibody. The antibody can recognize (specifically bind) a secreted protein from *S. citri* or *Candidatus Liberbacter*, wherein the secreted protein can indicated CSD or HLB, respectively.

Antibody reagents can be used in assays to detect the presence of, or protein expression levels, for the at least one secreted protein in a citrus sample using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.,* 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis,* 18:2184-93 (1997); Bao, *J. Chromatogr. B. Biomed. Sci.,* 699:463-80 (1997). Liposome immunoassays, such as flow-injection liposome immunoassays and liposome immunosensors, are also suitable for use in the present invention. See, e.g., Rongen et al., *J. Immunol. Methods,* 204:105-133 (1997). In addition, nephelometry assays, in which the formation of protein/antibody complexes results in increased light scatter that is converted to a peak rate signal as a function of the protein concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.,* 27:261-276 (1989)).

In some embodiments, the immunoassay includes a membrane-based immunoassay such as an dot blot or slot blot, wherein the biomolecules (e.g., proteins) in the sample are not first separated by electrophoresis. In such an assay, the sample to be detected is directly applied to a membrane (e.g., PVDF membrane, nylon membrane, nitrocellulose membrane, etc). Detailed descriptions of membrane-based immunoblotting are found in, e.g., Gallagher, S R. "Unit 8.3 Protein Blotting:Immunoblotting", *Current Protocols Essential Laboratory Techniques,* 4:8.3.1-8.3.36 (2010).

Specific immunological binding of the antibody to the protein of interest can be detected directly or indirectly. Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), in the physical form of sticks, sponges, papers, wells, and the like. An assay strip can be prepared by coating the antibody or a plurality of antibodies in an array on a solid support. This strip can then be dipped into the test sample and processed quickly through washes and detection steps to generate a measurable signal, such as a colored spot.

Comparative proteomic methods including mass spectrometry (MS) can be used to identify secreted proteins from pathogenic bacteria. For instance, secreted protein profiles from *S. citri* cells cultures with or without induction of citrus ploem extracts can be determined by MS. Genomic sequencing analysis can be performed to identify gene sequences encoding the secreted proteins. Protein sequence analysis can be used to determine the location of signal peptide cleavage sites based on the amino acid sequence. Secreted proteins for use in the method described herein can be identified using sequence analysis and bioinformatic prediction programs in diseased plants. Expression analysis can also be performed to confirm the presence of the secreted proteins. For instance, the probability of the protein being a Sec-secreted protein can be predicted from a protein's N-terminal secretion signal (e.g., a higher value indicates a greater probability).

Exemplary secreted proteins from *Spiroplasma citri* whose presence in a citrus sample is indicative of the pathogen (or the corresponding disease citrus stubborn disease) include, the protein Gene ID: CAK98563 or substantially identical variants. The amino acid sequence of CAK98563 (SEQ ID NO:1) is found in Uniprot No. Q14PL6. Additional secreted proteins from *Spiroplasma citri* include those described in Table 1 or substantially identical variants thereof. In some embodiments, a protein secreted from *S. citri*, including any one of those of Table 1, can be used in the method described herein as a detection marker for CSD.

TABLE 1

Secreted proteins from *Spiroplasma citri*

| SEQ ID NO: | Protein name | Probability of N-terminal secretion signal | Amino acid position of cleavage site |
|---|---|---|---|
| 1 | CAK98563 | 0.777 | 23 |
| 2 | CAK99824 | 0.843 | 23 |

TABLE 1-continued

Secreted proteins from *Spiroplasma citri*

| SEQ ID NO: | Protein name | Probability of N-terminal secretion signal | Amino acid position of cleavage site |
|---|---|---|---|
| 3 | CAK99227 | 0.998 | 29 |
| 4 | CAK99727 | 0.906 | 30 |
| 5 | CAL0019 | 0.75 | 27 |
| 6 | CAK98956 | 0.99 | 29 |
| 7 | P123-family protein variant A | | |
| 8 | P123-family protein variant B | | |

Exemplary secreted proteins from *Candidatus Liberibacter* asiaticus whose presence in a citrus sample is indicative of the pathogen (or the corresponding disease citrus greening disease, also known as Huanglongbing or HLB) include those described in Table 2 or substantially identical variants:

TABLE 2

Secreted proteins predicted from *Candidatus Liberibacter asiaticus*

| SEQ ID NO: | Protein Name | MW (kD) of mature protein | Protein function | Probability of N-terminal secretion signal |
|---|---|---|---|---|
| 9 | CLIBASIA_00460 | 9 | hypothetical protein | 0.667 |
| 10 | CLIBASIA_00995 | 35 | porin outer membrane protein | 0.55 |
| 11 | CLIBASIA_01135 | 33 | glycine betaine ABC transporter | 0.718 |
| 12 | CLIBASIA_01295 | 24 | flagellar L-ring protein | 0.637 |
| 13 | CLIBASIA_01300 | 17 | hypothetical protein | 0.546 |
| 14 | CLIBASIA_01600 | 35 | carboxypeptidase | 0.816 |
| 15 | CLIBASIA_03230 | 16 | hypothetical protein | 0.705 |
| 16 | CLIBASIA_03070 | 49 | pilus assembly protein | 0.723 |
| 17 | CLIBASIA_02610 | 45 | iron-regulated protein | 0.462 |
| 18 | CLIBASIA_02470 | 13 | putative secreted protein | 0.452 |
| 19 | CLIBASIA_02425 | 19 | outer membrane protein | 0.884 |
| 20 | CLIBASIA_02250 | 20 | extracellular solute-binding protein | 0.55 |
| 21 | CLIBASIA_02145 | 21 | hypothetical protein | 0.746 |
| 22 | CLIBASIA_02120 | 31 | periplasmic solute binding protein | 0.721 |
| 23 | CLIBASIA_04025 | 9 | hypothetical protein | 0.501 |
| 24 | CLIBASIA_04040 | 15 | hypothetical protein | 0.681 |
| 25 | CLIBASIA_04170 | 28 | rare lipoprotein A | 0.56 |
| 26 | CLIBASIA_04520 | 33 | hypothetical protein | 0.603 |
| 27 | CLIBASIA_04580 | 10 | hypothetical protein | 0.795 |
| 28 | CLIBASIA_05115 | 17 | hypothetical protein | 0.664 |
| 29 | CLIBASIA_05315 | 14 | hypothetical protein | 0.706 |
| 30 | CLIBASIA_00100 | 15 | ABC transporter protein | 0.588 |
| 31 | CLIBASIA_02075 | 44 | chemotaxis protein | 0.624 |
| 32 | CLIBASIA_03120 | 4 | hypothetical protein | 0.65 |
| 33 | CLIBASIA_04560 | 19 | hypothetical protein | 0.57 |
| 34 | CLIBASIA_05640 | 5 | hypothetical protein | 0.668 |
| 35 | CLIBASIA_05320 | 7 | hypothetical protein | 0.83 |

In some embodiments, a protein secreted from *S. citri*, including any one of those of Table 1, can be used in the method described herein as a detection marker for CSD.

Also provided are kits, e.g., for use in diagnostic and research applications. The kits can comprise any or all of the reagents to perform the methods described herein. The kits can also comprise a scalpel, razor blade or other implement for obtaining a plant or sap sample from a citrus tree. In addition, the kits can include instructional materials containing directions (i.e., protocols) for the practice of the methods. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

IV. Examples

This example illustrates a method for serological diagnosis of CSD using a *S. citri*-specific secreted protein ScCCPP1 which is CAK98563.

In the study, scCCPP1 was identified using mass spectrometry of the supernatant portion of a bacterial culture of *S. citri*. The protein was determined to be in relatively high abundance. Using an antibody generated against ScCCPP1 as the antigen, specific signals from *S. citri*-infected trees were detected using a direct tissue imprint assay. The results demonstrate that this method is suitable for field surveys.

Figure 1B:
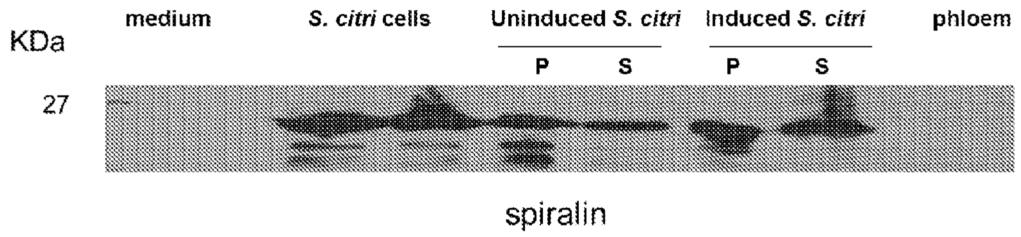
FIG. 1B shows that spiralin is present in all samples containing *S. citri.*

Western blot analysis with rabbit polyclonal anti-ScCCPP1 antibody showed that the secreted pathogen protein was present in the total protein extracts harvested from *S. citri* cells. ScCCPP1 was also detect uninduced *S. citri* cells in phloem extracts, as well as induced *S. citri* cells in either phloem extracts or sucrose only (FIG. 1A). For comparison, spiralin protein which is a major membrane protein of *Spiroplasma citri* was detected at high levels in the cells including those uninduced and induced (FIG. 1B).

Figure 2:
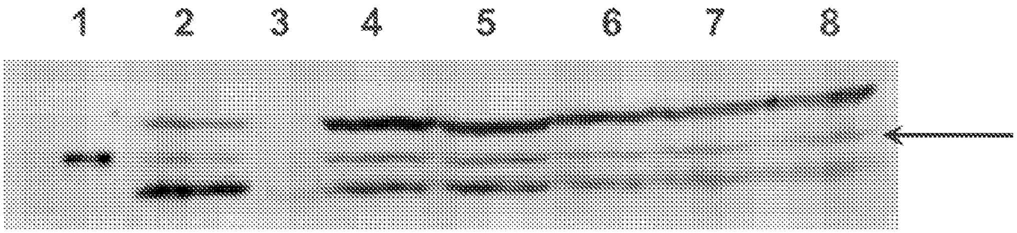
FIG. 2 illustrates Western blot analysis of ScCCPP1 protein in *S. citri* cells, grafting-inoculated plant tissue and CSD-infected trees from the field.

Western blot analysis, as shown in FIG. 2, indicated that ScCCPP1 protein was detected in a protein extract sample from a citrus seedling that was graft-inoculated with *Spiroplasma citri* (lane 2) or extract samples from CSD-infected adult trees from the field (lane 4-8). Protein extract from *S. citri* cells (lane 1) was used as a positive control. Protein extract sample from a healthy citrus tree (lane 3) was used as a negative control. The arrowhead of FIG. 2 indicates the position of the predicted MW of ScCCPP1.

In a simple imprint assay, samples of process-free sap from leaves or young branches were obtained from *S. citri*-infected trees. The plant tissues were removed from the adult trees using a razor blade. The samples were "printed" on a nitrocellulose membrane by pressing the freshly cut cross section of leaf petioles or branches on the membrane, which left faint green-colored marks from the sap in the samples. The membranes were then be taken back to the lab and incubated with a rabbit anti-ScCCPP1 polyclonal antibody for one hour at room temperature (about 22° C.). The membranes were washed with a wash solution to remove any unbound primary antibody. A secondary antibody recognizing rabbit antibodies and conjugated with HRP was added to the membranes and incubated for one hour at room temperature (about 22° C.). The membranes were washed with a wash solution to remove any unbound secondary antibody. Detection was performed using a chemiluminescent reagent and standard autoradiography technique.

Figure 3A:
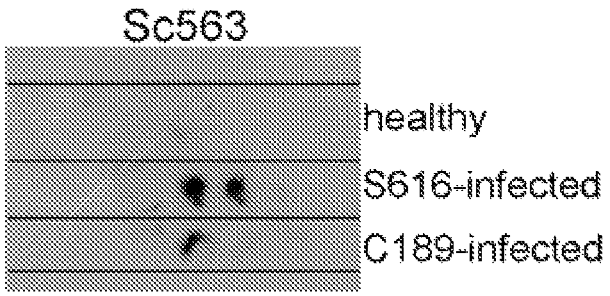
FIG. 3A illustrates that the anti-ScCCPP1 antibody specifically detects *S. citri* using leaf petiole imprints.
Figure 3B:
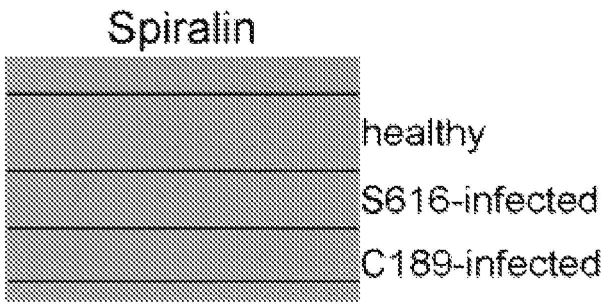
FIG. 3B shows that spiralin protein was not detected in the same samples using the spiralin antibody of FIG. 1B.

Citrus trees that were graft-infected with two *S. citri* strains (S616 and C189) were examined using an antibody against ScCCPP1 or an antibody against spiralin. ScCCPP1 was detected in imprinted leaf petiole samples from S616-infected trees and C189-infected trees (FIG. 3A). Surprisingly, the spiralin antibody failed to give positive signals from the same samples (FIG. 3B). The results demonstrate that ScCCPP1 can be used as a detection marker for CSD, even in plant samples that do not contain bacterial pathogen cells.

Figures 4A, 4B:
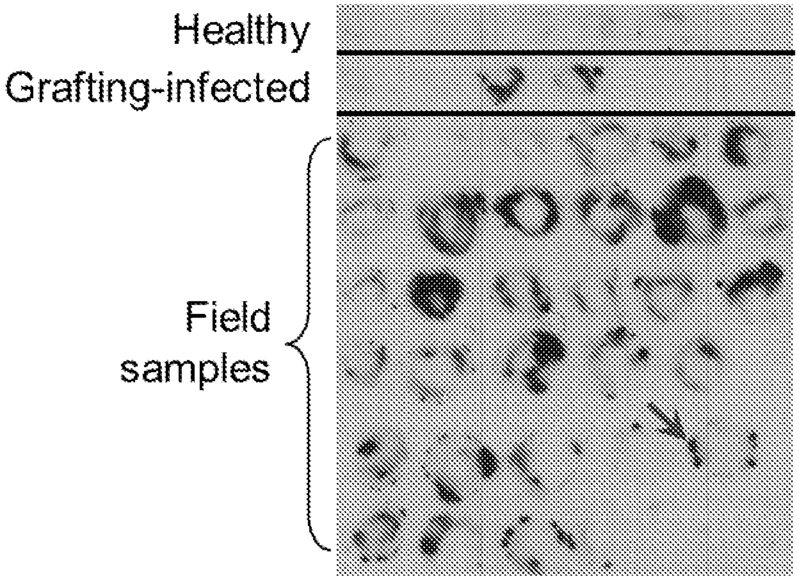
FIG. 4A shows an exemplary membrane-based immunoassay or imprinting assay performed on samples harvested from the field.
FIG. 4B shows that the imprinting assay is more sensitive than quantitative PCR for detecting CSD.

Strong signals of ScCCPP1 were observed in imprints of phloem-rich tissues (e.g., barks) from *S. citri*-infected citrus trees in the field (FIG. 4A). Four to six different young branches from each tree were printed on the same row of the membrane. Six CSD-infected trees from the field were tested. The arrowhead in FIG. 4 points to a positive signal present exclusively in the regions corresponding to the phloem-rich tissues (e.g., barks) of a branch. This represents the location of the bacterium and the secreted protein. Positive signal was not seen in all tested branches, thus indicating the sporadic distribution of the disease.

Comparison of the imprint method to a nucleic acid-based quantitative PCR (Q-PCR) assay showed that the imprinting immunoassay provides more consistent and more robust detection of CSD infection (FIG. 4B). Young branches from healthy (negative control), graft-inoculated (positive control), and nine field trees were tested by Q-PCR and imprinting immunoassay. Field sample 2 and 5 appeared to be negative for CAK98563 and positive for spiralin by Q-PCR, indicating that the pathogen was absent from these samples. However, the imprint results show that the same samples were actually positive for ScCCPP1 and thus CSD. The data demonstrate that the imprint assay using the ScCCPP1 antibody provides more consistent and robust detection compared to quantitative PCR.

The results also show that the positive signals were mainly present from the regions corresponding to the phloem-rich tissues. This is consistent with the primary location of the antigen. Remarkably, the anti-ScCCPP1 polyclonal antibody gave more reliable and consistent results than an antibody against spiralin protein, which is a major cell membrane component of the bacterial pathogen and one of the most abundant proteins of present in *S. citri*. These data demonstrate that the presence of CAK98563 indicates citrus stubborn disease in plants even in the absence of *S. citri* cells. The results also confirm that pathogen secreted proteins can be used as detection markers for phloem-limited bacterial diseases of citrus.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of detecting the presence of CLIBASIA_05315 protein (SEQ ID NO:29) in a citrus plant, the method comprising:

obtaining sap from the citrus plant;

contacting the sap with an antibody that specifically binds the protein consisting of SEQ ID NO:29;

detecting the presence or absence of specific binding of the antibody to SEQ ID NO:29 in the sap, thereby detecting the presence or absence of SEQ ID NO:29 in the citrus plant; and destroying the citrus plant when SEQ ID NO:29 is detected in the citrus plant.

2. The method of claim 1, wherein the citrus plant is not artificially infected or grafting-inoculated with a bacterial pathogen.

3. The method of claim 1, wherein samples of sap from a plurality of citrus plants are screened by the method.

4. The method of claim 1, wherein the sap is applied to a membrane and the detecting of binding comprises contacting the antibody to the membrane.

5. The method of claim 1, wherein the antibody is linked to a solid support.

6. The method of claim 1, wherein the sap is unpurified.

* * * * *